US008905023B2

(12) United States Patent
Niland et al.

(10) Patent No.: US 8,905,023 B2
(45) Date of Patent: Dec. 9, 2014

(54) HYPERTHERMIC HUMIDIFICATION SYSTEM

(75) Inventors: William F. Niland, Arnold, MD (US); Owen S. Bamford, Linthicum, MD (US); Felino V. Cortez, Jr., Bowie, MD (US)

(73) Assignee: Vapotherm, Inc., Exeter, NH (US)

( * ) Notice: Subject to any disclaimer, the term of this patent is extended or adjusted under 35 U.S.C. 154(b) by 1872 days.

(21) Appl. No.: 11/973,061

(22) Filed: Oct. 5, 2007

(65) Prior Publication Data
US 2009/0090363 A1   Apr. 9, 2009

(51) Int. Cl.
| A61M 16/16 | (2006.01) |
| A61M 16/10 | (2006.01) |
| A61M 16/20 | (2006.01) |
| A61M 16/12 | (2006.01) |
| A61M 11/00 | (2006.01) |
| A61M 11/04 | (2006.01) |
| A61M 16/00 | (2006.01) |
| A61M 5/36 | (2006.01) |
| A61M 16/06 | (2006.01) |

(52) U.S. Cl.
CPC ....... *A61M 16/16* (2013.01); *A61M 2205/3382* (2013.01); *A61M 2202/0225* (2013.01);
(Continued)

(58) Field of Classification Search
USPC ............. 128/203.16–203.17, 203.25–203.27, 128/204.14, 204.17–204.18, 204.21–204.23
See application file for complete search history.

(56) References Cited

U.S. PATENT DOCUMENTS

| 2,742,040 A | 4/1956 | Moore et al. |
| 3,108,147 A | 10/1963 | Flury |

(Continued)

FOREIGN PATENT DOCUMENTS

| DE | 28 43 756 | 4/1980 |
| DE | 103 17 268 | 11/2004 |

(Continued)

OTHER PUBLICATIONS

Partial International Search Report for International Application No. PCT/US2007/021469 dated Jul. 10, 2008.

(Continued)

*Primary Examiner* — Valerie L Skorupa
(74) *Attorney, Agent, or Firm* — Ropes & Gray LLP

(57) ABSTRACT

Apparatus and methods for delivering humidified breathing gas to a patient are provided. The apparatus includes a humidification system configured to deliver humidified breathing gas to a patient. The humidification system includes a vapor transfer unit and a base unit. The vapor transfer unit includes a liquid passage, a breathing gas passage, and a vapor transfer device positioned to transfer vapor to the breathing gas passage from the liquid passage. The base unit includes a base unit that releasably engages the vapor transfer unit to enable reuse of the base unit and selective disposal of the vapor transfer unit. The liquid passage is not coupled to the base unit for liquid flow therebetween when the vapor transfer unit is received by the base unit.

22 Claims, 28 Drawing Sheets

(52) U.S. Cl.
CPC ... *A61M 16/1075* (2013.01); *A61M 2016/1025* (2013.01); *A61M 2016/0039* (2013.01); *A61M 2202/0208* (2013.01); *A61M 2205/3386* (2013.01); *A61M 16/203* (2014.02); *A61M 5/365* (2013.01); *A61M 16/209* (2014.02); *A61M 2205/8212* (2013.01); *A61M 2205/18* (2013.01); *A61M 2205/6072* (2013.01); *A61M 16/0666* (2013.01); *A61M 2205/8262* (2013.01); *A61M 16/109* (2014.02); *A61M 2205/3313* (2013.01); *A61M 2209/08* (2013.01); *A61M 16/162* (2013.01); *A61M 16/12* (2013.01); *A61M 2016/0027* (2013.01); *A61M 2205/502* (2013.01); *A61M 2202/025* (2013.01); *A61M 2205/14* (2013.01); *A61M 2205/70* (2013.01); *A61M 2202/0275* (2013.01); *A61M 11/006* (2013.01); *A61M 2205/3368* (2013.01); *A61M 2205/3331* (2013.01); *A61M 2205/123* (2013.01); *A61M 11/042* (2014.02)
USPC ............ 128/203.26; 128/203.16; 128/203.17; 128/203.27; 128/203.12

(56) References Cited

U.S. PATENT DOCUMENTS

| | | | |
|---|---|---|---|
| 3,650,093 A | 3/1972 | Rosenberg | |
| 3,659,604 A | 5/1972 | Melville et al. | |
| 3,871,373 A * | 3/1975 | Jackson | 128/203.27 |
| 3,982,095 A | 9/1976 | Robinson | |
| 4,013,742 A | 3/1977 | Lang | |
| 4,028,444 A | 6/1977 | Brown et al. | |
| 4,028,445 A | 6/1977 | Hickmann et al. | |
| 4,036,919 A | 7/1977 | Komendowski et al. | |
| 4,051,205 A * | 9/1977 | Grant | 261/70 |
| 4,098,853 A * | 7/1978 | Brown et al. | 261/122.1 |
| 4,110,419 A | 8/1978 | Miller | |
| 4,172,105 A | 10/1979 | Miller et al. | |
| 4,203,027 A | 5/1980 | O'Hare et al. | |
| 4,276,236 A | 6/1981 | Sullivan et al. | |
| 4,303,601 A | 12/1981 | Grimm et al. | |
| 4,323,064 A | 4/1982 | Hoenig et al. | |
| 4,338,267 A | 7/1982 | Riuli et al. | |
| 4,354,984 A | 10/1982 | Richardson et al. | |
| 4,366,105 A | 12/1982 | Nowacki | |
| 4,369,777 A | 1/1983 | Lwoff et al. | |
| 4,401,114 A | 8/1983 | Lwoff et al. | |
| 4,430,994 A | 2/1984 | Clawson | |
| 4,453,542 A | 6/1984 | Hughes | |
| 4,500,480 A | 2/1985 | Cambio, Jr. | |
| 4,563,313 A | 1/1986 | Tsuaki | |
| 4,589,409 A | 5/1986 | Chatburn et al. | |
| 4,606,866 A | 8/1986 | McGlothlin et al. | |
| 4,621,632 A | 11/1986 | Bartels et al. | |
| 4,621,633 A | 11/1986 | Bowles et al. | |
| 4,630,475 A | 12/1986 | Mizoguchi | |
| 4,644,790 A | 2/1987 | Mizoguchi | |
| 4,657,713 A | 4/1987 | Miller | |
| 4,682,010 A | 7/1987 | Drapeau et al. | |
| 4,715,998 A | 12/1987 | Clow | |
| 4,753,758 A * | 6/1988 | Miller | 261/139 |
| 4,765,327 A | 8/1988 | Shim | |
| 4,810,854 A | 3/1989 | Jursich et al. | |
| 4,832,012 A | 5/1989 | Raabe et al. | |
| 4,844,072 A | 7/1989 | French et al. | |
| 4,921,642 A * | 5/1990 | LaTorraca | 261/142 |
| 4,941,469 A * | 7/1990 | Adahan | 128/205.18 |
| 4,943,704 A | 7/1990 | Rabenau et al. | |
| 4,957,107 A * | 9/1990 | Sipin | 128/204.21 |
| 4,967,741 A | 11/1990 | Cambio, Jr. | |
| 4,973,231 A * | 11/1990 | Colliver | 417/369 |
| 5,038,840 A | 8/1991 | Fair | |
| 5,109,471 A | 4/1992 | Lang | |
| 5,158,584 A | 10/1992 | Tamura | |
| 5,195,515 A | 3/1993 | Levine | |
| 5,255,674 A | 10/1993 | Oftedal et al. | |
| 5,259,062 A | 11/1993 | Pelonis | |
| 5,329,939 A | 7/1994 | Howe | |
| 5,336,156 A | 8/1994 | Miller et al. | |
| 5,349,946 A | 9/1994 | McComb | |
| 5,392,770 A | 2/1995 | Clawson et al. | |
| 5,431,885 A | 7/1995 | Zlotnik et al. | |
| 5,445,143 A | 8/1995 | Sims | |
| 5,454,368 A | 10/1995 | Tarulli | |
| 5,529,060 A | 6/1996 | Salmon et al. | |
| 5,549,720 A | 8/1996 | Miller et al. | |
| 5,572,992 A * | 11/1996 | Kankkunen et al. | 128/203.14 |
| 5,577,494 A * | 11/1996 | Kuypers et al. | 128/201.13 |
| 5,590,648 A | 1/1997 | Mitchell et al. | |
| 5,724,957 A | 3/1998 | Rubsamen et al. | |
| 5,769,071 A * | 6/1998 | Turnbull | 128/203.12 |
| 5,857,062 A | 1/1999 | Bergamaschi et al. | |
| 6,004,385 A | 12/1999 | Birmingham | |
| 6,010,118 A | 1/2000 | Milewicz | |
| D421,298 S | 2/2000 | Kenyon et al. | |
| 6,032,930 A | 3/2000 | Calino | |
| 6,041,777 A | 3/2000 | Faithfull et al. | |
| 6,050,260 A | 4/2000 | Daniell | |
| 6,050,552 A | 4/2000 | Loescher et al. | |
| 6,095,505 A | 8/2000 | Miller | |
| 6,142,971 A | 11/2000 | Daoud et al. | |
| 6,167,883 B1 | 1/2001 | Beran et al. | |
| 6,216,691 B1 | 4/2001 | Kenyon et al. | |
| 6,397,841 B1 | 6/2002 | Kenyon et al. | |
| 6,481,437 B1 | 11/2002 | Pate | |
| 6,510,848 B1 | 1/2003 | Gibertoni | |
| 6,523,810 B2 | 2/2003 | Offir et al. | |
| 6,536,430 B1 | 3/2003 | Smith | |
| 6,554,260 B1 | 4/2003 | Lipscombe et al. | |
| 6,560,408 B2 | 5/2003 | Glucksman et al. | |
| 6,613,280 B2 | 9/2003 | Myrick et al. | |
| 6,718,974 B1 | 4/2004 | Moberg | |
| 6,769,430 B1 | 8/2004 | Carlsen et al. | |
| 6,772,756 B2 | 8/2004 | Shayan | |
| 6,827,046 B2 | 12/2004 | Welle | |
| 6,827,084 B2 | 12/2004 | Grubb, Jr. | |
| 6,877,510 B2 | 4/2005 | Nitta | |
| 6,904,911 B2 | 6/2005 | Gibertoni | |
| 6,912,977 B2 * | 7/2005 | Cumming | 123/3 |
| 6,938,886 B2 | 9/2005 | Glucksman | |
| 6,953,354 B2 | 10/2005 | Edirisuriya et al. | |
| 6,956,190 B2 | 10/2005 | Sano et al. | |
| 6,988,497 B2 | 1/2006 | Levine | |
| 6,997,183 B2 | 2/2006 | Koch et al. | |
| 6,997,185 B2 | 2/2006 | Han et al. | |
| 7,051,733 B2 | 5/2006 | Gradon et al. | |
| 7,066,452 B2 | 6/2006 | Rotering et al. | |
| 7,111,624 B2 | 9/2006 | Thudor et al. | |
| 7,306,205 B2 * | 12/2007 | Huddart et al. | 261/130 |
| 7,380,774 B2 * | 6/2008 | Akita et al. | 261/104 |
| 7,428,902 B2 * | 9/2008 | Du et al. | 128/204.17 |
| 7,571,725 B2 * | 8/2009 | Wickham et al. | 128/204.18 |
| 2001/0056258 A1 * | 12/2001 | Evans | 604/131 |
| 2002/0000225 A1 | 1/2002 | Schueler et al. | |
| 2002/0148471 A1 | 10/2002 | Hirabayashi | |
| 2003/0098022 A1 | 5/2003 | Nakao et al. | |
| 2003/0126691 A1 | 7/2003 | Gerlach et al. | |
| 2003/0209246 A1 | 11/2003 | Schroeder et al. | |
| 2004/0221854 A1 | 11/2004 | Hete et al. | |
| 2004/0234254 A1 | 11/2004 | Czupich et al. | |
| 2005/0133942 A1 | 6/2005 | Schuld | |
| 2005/0166915 A1 | 8/2005 | Gibertoni | |
| 2005/0169615 A1 | 8/2005 | Glucksman | |
| 2006/0012057 A1 | 1/2006 | Anthony | |
| 2006/0124127 A1 | 6/2006 | Du et al. | |
| 2006/0191531 A1 | 8/2006 | Mayer et al. | |
| 2006/0222347 A1 | 10/2006 | Wefler et al. | |
| 2006/0243804 A1 | 11/2006 | Christofferson et al. | |
| 2007/0137646 A1 * | 6/2007 | Weinstein et al. | 128/204.17 |
| 2007/0175473 A1 | 8/2007 | Lewis et al. | |

(56) References Cited

U.S. PATENT DOCUMENTS

| | | | |
|---|---|---|---|
| 2007/0283958 A1* | 12/2007 | Naghavi | 128/204.18 |
| 2008/0078386 A1* | 4/2008 | Feldhahn et al. | 128/204.18 |
| 2010/0133292 A1* | 6/2010 | Ware et al. | 222/1 |

FOREIGN PATENT DOCUMENTS

| | | |
|---|---|---|
| GB | 1448473 | 9/1976 |
| WO | WO 99/47197 | 9/1999 |
| WO | WO 03/035157 | 5/2003 |
| WO | WO 2004/096315 | 11/2004 |
| WO | WO 2006024292 A1 * | 3/2006 |
| WO | WO 2007/038152 | 4/2007 |

OTHER PUBLICATIONS

International Search Report for International Application No. PCT/US2007/021469 dated Oct. 13, 2008.

Written Opinion of the International Searching Authority for International Application No. PCT/US2007/021469 dated Oct. 13, 2008.

Vapotherm, the new standard in high flow therapy brochure, 6 pp., undated.

* cited by examiner

HYPERTHERMIC HUMIDIFICATION SYSTEM

FIELD OF THE INVENTION

This invention relates to apparatus and methods for respiratory tract therapy. More particularly, this invention relates to an apparatus configured to deliver heated and humidified breathing gas to a patient.

BACKGROUND OF THE INVENTION

Respiratory airway therapies are recognized medical treatments that enhance breathing by delivering breathing gas to the respiratory tract of patients. Respiratory devices such as humidifier/ventilator systems, however, include parts that may be at risk of contamination due to contact with water or water vapor. While disinfection protocols have been developed to minimize and control bacterial growth, there remains a need for an improved apparatus for respiratory tract therapy that can be used in various settings including clinical and hospital settings that reduces the risk of bacterial contamination. There also remains a need for improved methods of respiratory airway therapy.

SUMMARY OF THE INVENTION

In one aspect, the invention provides a humidification system configured to deliver humidified breathing gas to a patient. The humidification system includes a vapor transfer unit and a base unit. The vapor transfer unit includes a liquid passage, a breathing gas passage, and a vapor transfer device positioned to transfer vapor to the breathing gas passage from the liquid passage. The system includes a base unit that releasably engages the vapor transfer unit to enable reuse of the base unit and selective disposal of the vapor transfer unit. The liquid passage is not coupled to the base unit for liquid flow therebetween when the vapor transfer unit is received by the base unit.

In another aspect, the humidification system configured to deliver humidified breathing gas to a patient includes a vapor transfer unit and a base unit. The vapor transfer unit includes a liquid passage, a breathing gas passage, and a vapor transfer device positioned to transfer vapor to the breathing gas passage from the liquid passage. The base unit releasably engages the vapor transfer unit. The base unit has at least one sensor positioned to sense a parameter in the liquid passage of the vapor transfer device.

In yet another aspect, the humidification system configured to deliver humidified breathing gas to a patient includes a vapor transfer unit and a base unit. The vapor transfer unit has a liquid passage and a first pump portion positioned to advance liquid through the liquid passage. The base unit releasably engages with the vapor transfer unit. The base unit has a second pump portion adapted to operationally mate with the first pump portion to advance liquid through the liquid passage of the vapor transfer unit when the base unit engages the vapor transfer unit.

In still another aspect, the humidification system is configured to deliver heated and humidified breathing gas to a patient and includes a vapor transfer unit and a base unit. The vapor transfer unit has a liquid passage and a first heater portion positioned to heat liquid in the liquid passage. The base unit releasably engages the vapor transfer unit to enable reuse of the base unit and selective disposal of the vapor transfer unit. The liquid passage is not coupled to the base unit for liquid flow therebetween when the vapor transfer unit is received by the base unit. The base unit has a second heater portion adapted to conduct heat to the first heater portion to heat liquid in the liquid passage of vapor transfer unit.

In still yet another aspect, the invention provides a vapor transfer unit for use with a base unit of a humidification system for delivering heated and humidified breathing gas to a patient. The vapor transfer unit is configured to be releasably mounted to base unit to accommodate reuse of base unit and selective disposal of vapor transfer unit. The vapor transfer unit includes liquid and breathing gas passages and a vapor transfer device is positioned to transfer vapor to the breathing gas passage from the liquid passage. An impeller is positioned to advance liquid through the liquid passage and a sensor is positioned to sense a level of liquid in the liquid passage.

BRIEF DESCRIPTION OF THE DRAWINGS

The invention is best understood from the following detailed description when read in connection with the accompanying drawings, with like elements having the same reference numerals. This emphasizes that according to common practice, the various features of the drawings are not drawn to scale. On the contrary, the dimensions of the various features are arbitrarily expanded or reduced for clarity. Included in the drawings are the following figures.

DETAILED DESCRIPTION OF THE INVENTION

Figure 1:
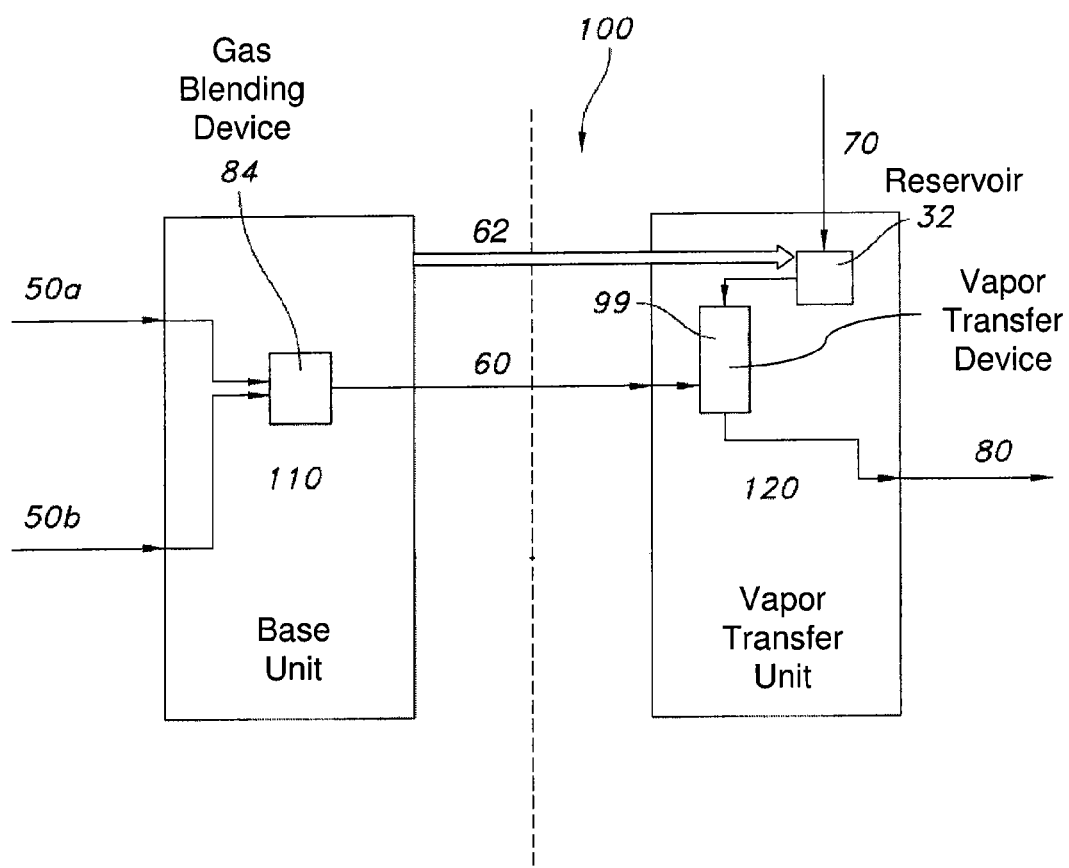
FIG. 1 is a schematic representation of a humidification system according to an exemplary aspect of this invention.

Aspects of the invention will now be described with reference to the figures. Such figures are intended to be illustrative rather than limiting and are included herewith to facilitate the explanation of the present invention.

Humidification System

Referring generally to the figures (FIGS. 1-14), in accordance with an exemplary embodiment, the invention provides a humidification system 100 to deliver heated and humidified breathing gas 80 to a patient. Humidification system 100 includes a base unit 110 and a vapor transfer unit, or fluid pathway module, 120. Base unit 110 may include controls for operating humidification system 100 and is configured to operate without liquid flowing through base unit 110 or being exchanged with fluid pathway module 120. Fluid pathway module 120 is releasably mounted to base unit 110 and is configured to operate with liquid 70, such as water, flowing through fluid pathway module 120 (but not base unit 110) to allow reuse of base unit 110 and selective disposal of fluid pathway module 120. Thus, cost savings and lowered contamination risk for humidification system 100 can be realized through reuse of base unit 110 and by periodically changing fluid pathway module (e.g., for each patient and/or at a determined time interval), which is the component that contacts the water and water vapor, and therefore more prone to bacterial contamination.

Referring now to the individual figures in detail, FIG. 1 illustrates a schematic representation of humidification system 100. Humidification system 100 manages the delivery of heated and humidified breathing gas 80 to the patient and includes base unit 110 and fluid pathway module 120. The illustrated base unit 110 includes the controls for operating humidification system 100 and is configured to receive breathing gas 50a, 50b, such as medical air and oxygen, respectively. Alternatively, the controls may be remote to base unit 110. In addition, other gases, such as, for example, helium, nitric oxide (INO), carbon dioxide, and/or other gases, may be used. For gases other than air and oxygen, base unit 110 may need to be recalibrated for the specific gases being used. When different types of gas are received through base unit 110, gases 50a, 50b may be blended by gas blending device 84, to form blended gas 60, which is delivered to fluid pathway module 120. While two different gases may be used with system 100, those skilled in the art will recognize that system 100 may be used with only one gas, such as, for example pure oxygen or air, in which case gas blending device 84 may be omitted.

Fluid pathway module 120 is releasably mounted to base unit 110 and is configured to receive gas 60 from base unit 110 and liquid 70 from an external water source. In an exemplary embodiment, liquid 70 received by fluid pathway module 120 is contained in a reservoir 32 to minimize potential contamination of base unit 110 and to prime a pump used to circulate liquid 70. Liquid 70 contained in reservoir 32 may be heated by heat conduction 62 from base unit 110. Vapor transfer device 99 releasably mounted to fluid pathway module 120 combines liquid 70 from reservoir 32 and blended gas 60 to supply heated and humidified breathing gas 80 to a patient.

Base Unit

Referring now to FIGS. 2, 3A, 3B, and 4, an exemplary embodiment of humidification system 100 according to the present invention is illustrated. Humidification system 100 includes base unit 110, which contains the controls that operate humidification system 100 and is configured to operate without liquid flowing internally through base unit 110 or being exchanged with fluid pathway module 120. In the exemplary embodiment, base unit 110 is completely dry so that potential damage to electronics that control humidification system 100 and bacterial contamination of base unit 110 is minimized.

Figure 4:
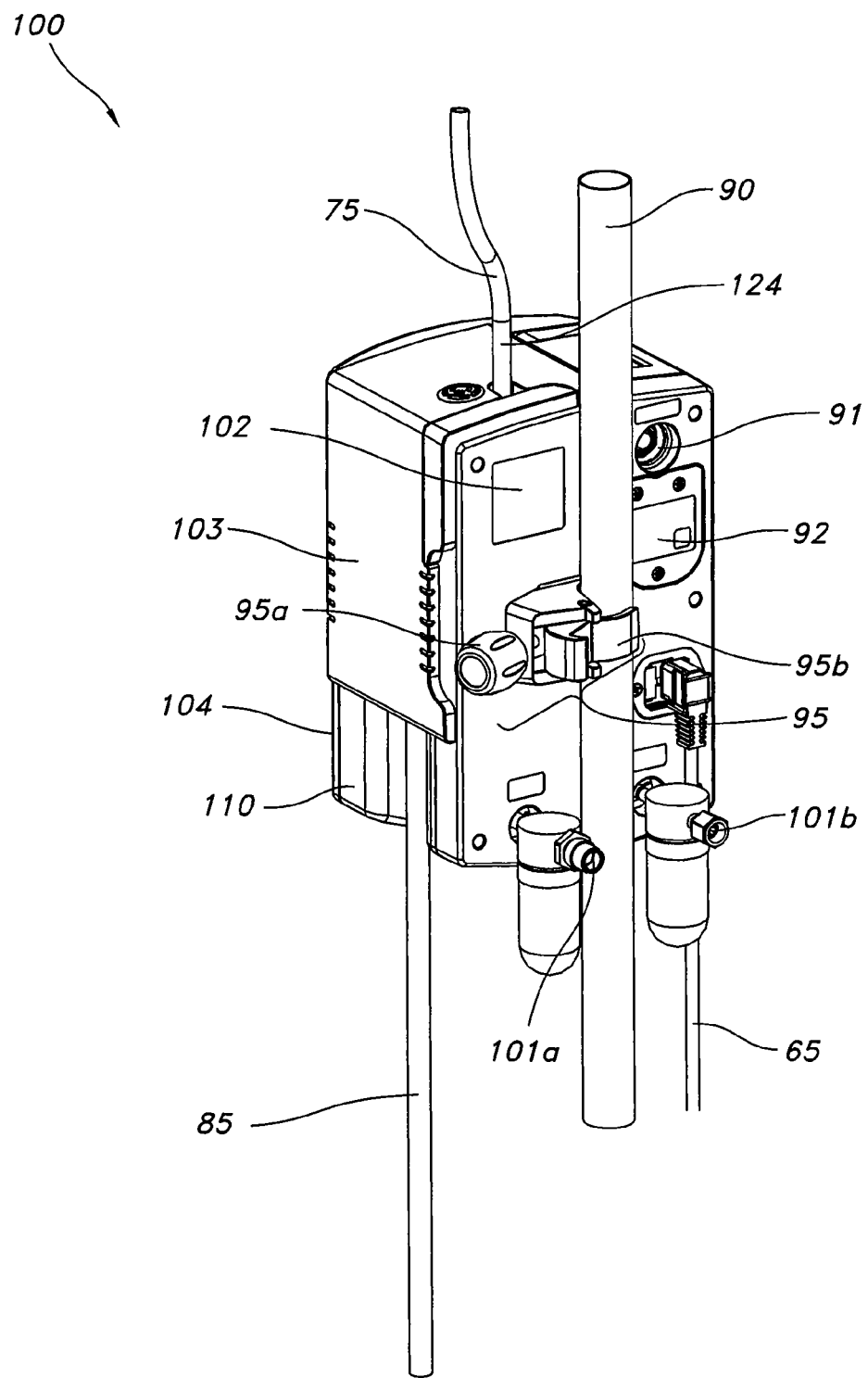
FIG. 4 is rear perspective view of the humidification system shown in FIG. 2.

Base unit 110 is mountable to a stand 90, such as an IV pole, via mounting mechanism 95, shown in FIG. 4. In an exemplary embodiment, rear panel 102 of base unit 110 includes a bracket 95b and a knob 95a that manipulates bracket 95b to releasably secure base unit 110 to stand 90. When knob 95a is rotated, for example, bracket 95b may be tightened or loosened on stand 90, thereby securing or loosening humidification system 100 with respect to stand 90.

The rear of base unit 110, best illustrated in FIG. 4, further includes gas inlet ports with filters 101a, 101b that are configured to connect to gas supply lines (not shown). The gas supply lines supply gas (such as medical air and oxygen) from a portable tank, compressor, or wall outlet into base unit 110. In an exemplary embodiment, gas supplied to base unit 110 may be filtered and blended to provide a contaminant-free gas mixture. A gas blending device (not shown in FIGS. 2-4), for example, may be installed within base unit 110 to blend the gas being supplied into base unit 110. Additional aspects of the gas blending device and gas blending operation will be described in further detail below.

Figure 2:
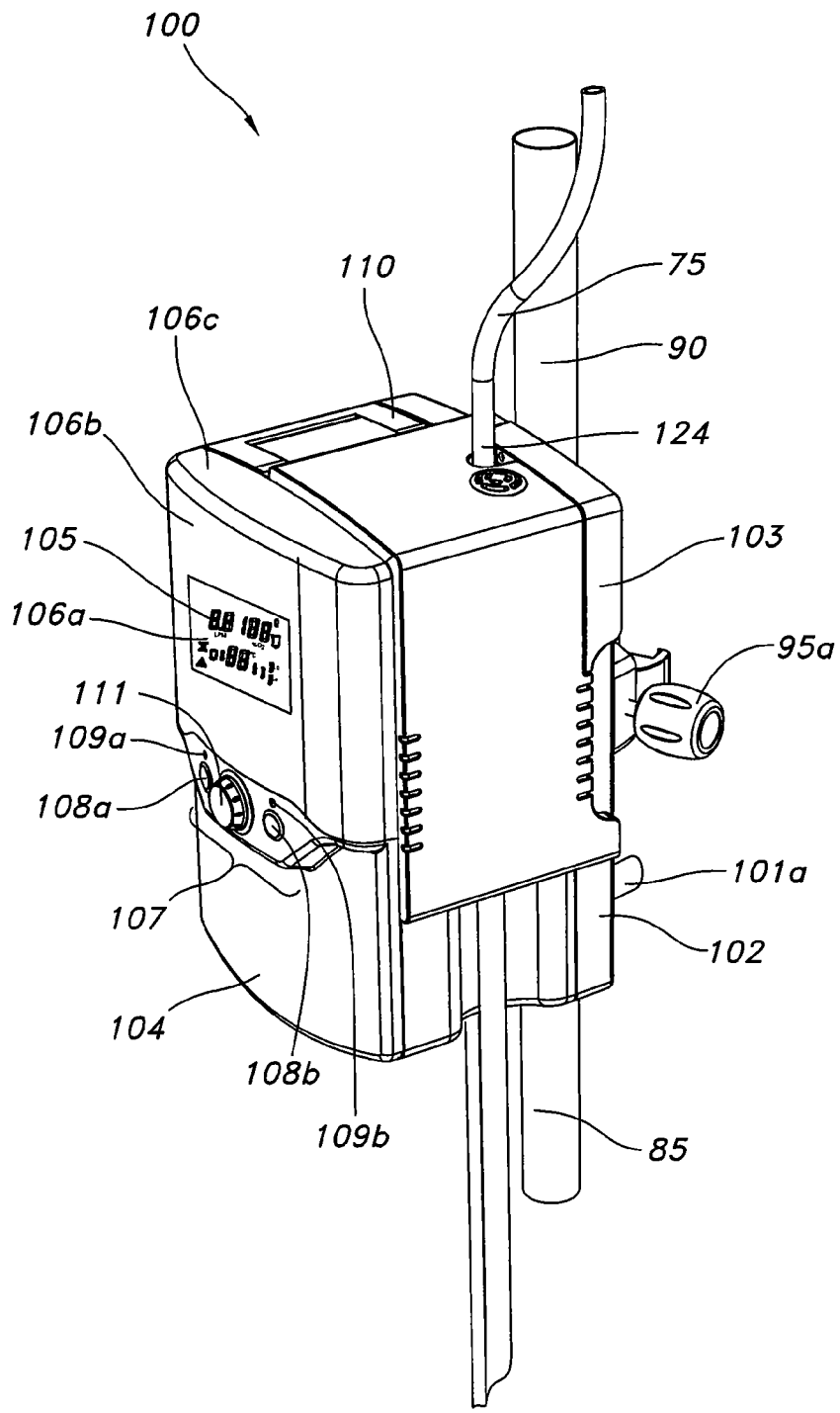
FIG. 2 is a front perspective view of an exemplary embodiment of the humidification system in accordance with the present invention.
Figure 3A:
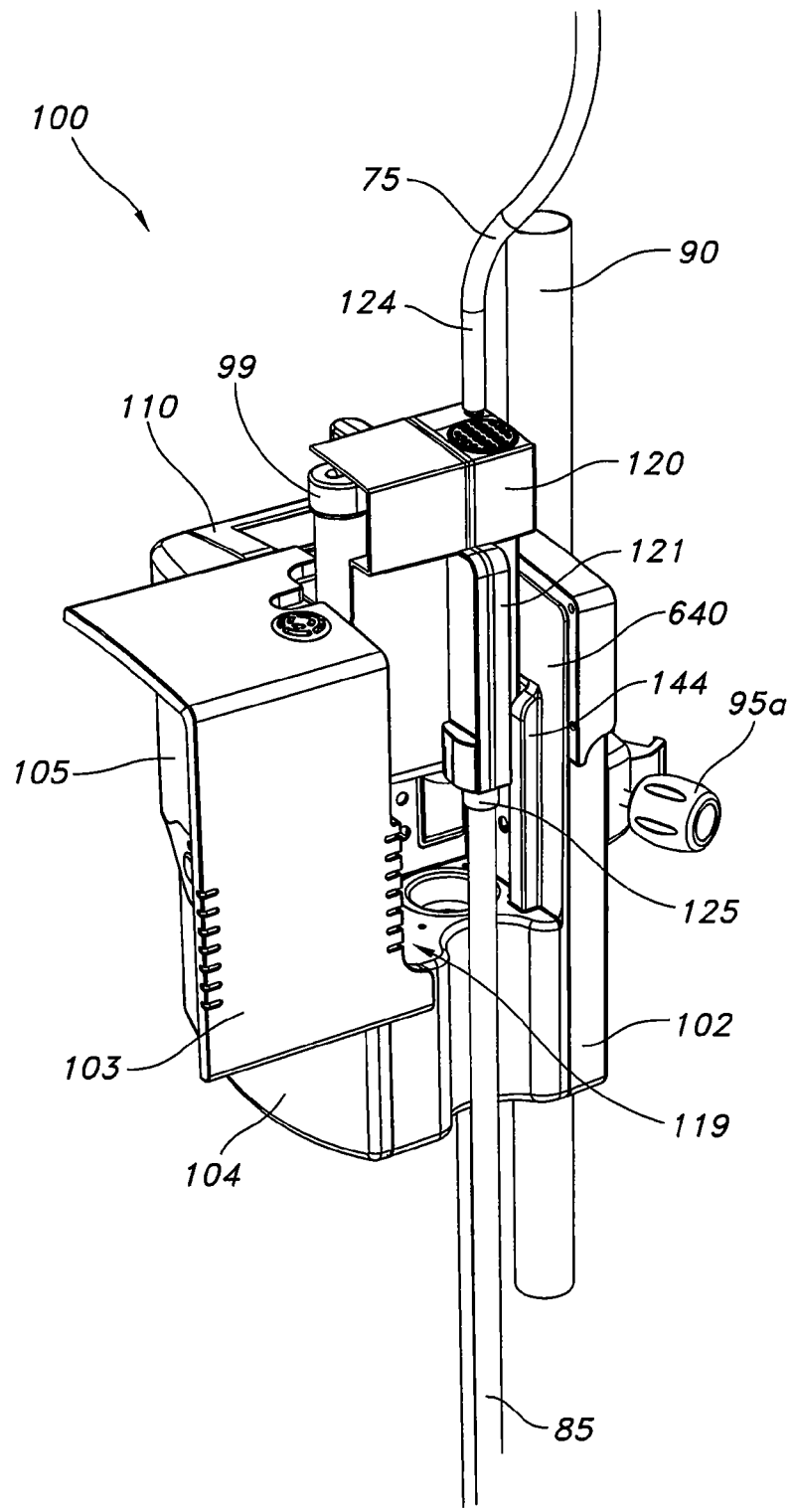
FIG. 3A is a side perspective view of the humidification system shown in FIG. 2, with a vapor transfer cartridge partially inserted into a base unit.
Figure 3B:
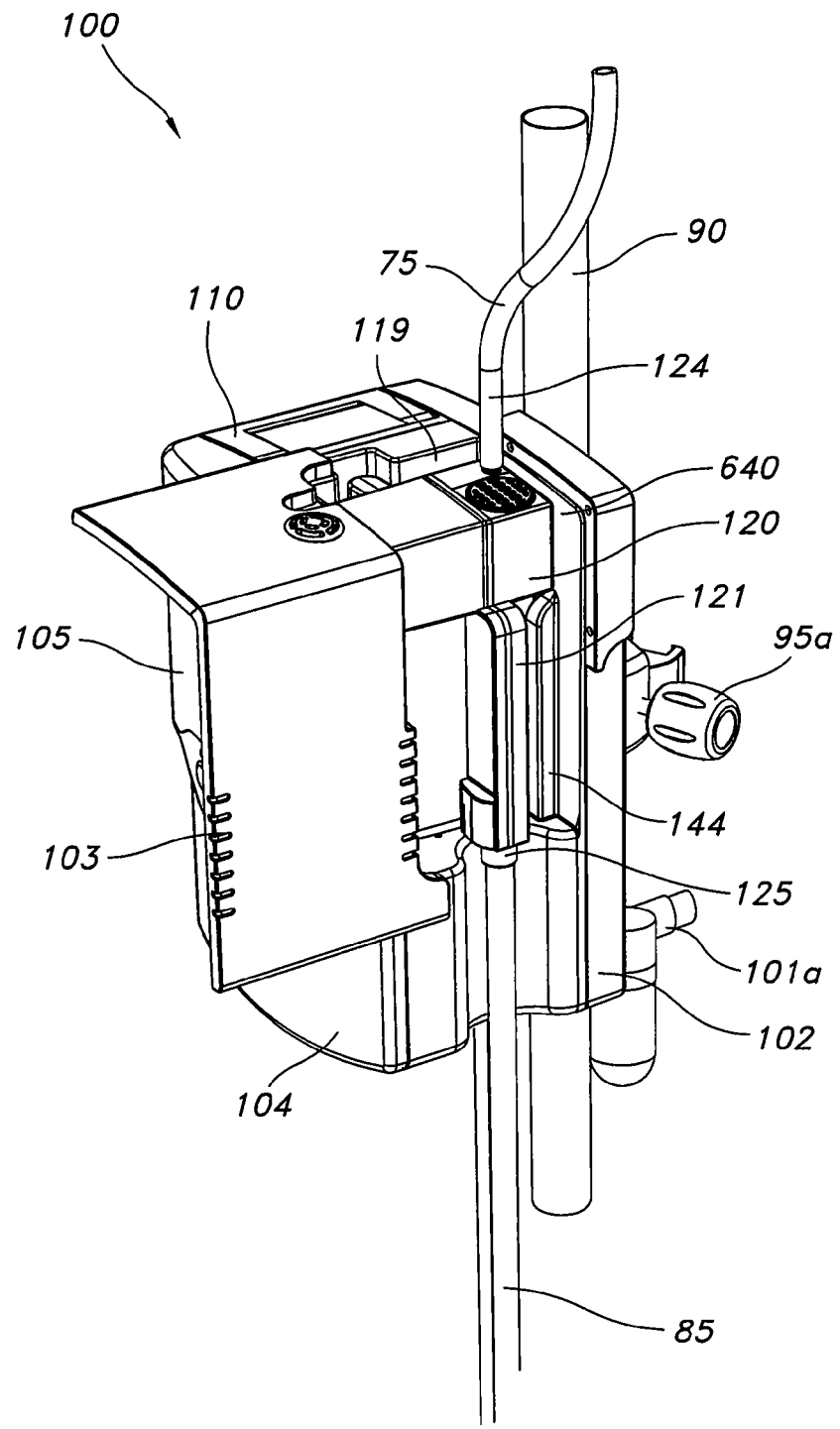
FIG. 3B is a side perspective view of the humidification system shown in FIG. 2, with the vapor transfer cartridge fully inserted into the base unit.

The side of base unit 110, best illustrated in FIGS. 2-4, includes a door 103 that may be slid open or closed to expose or cover a component receiving portion 119 of base unit 110. As shown in FIGS. 2 and 4, door 103 may be slid completely closed to cover the component receiving portion 119 from view. As illustrated in FIGS. 3A and 3B, door 103 is slid open to expose component receiving portion 119 of base unit 110. When door 103 is open, fluid pathway module 120 can be releasably mounted or removed from component receiving portion 119, e.g., using a handle 121. A guide 144 extends from the side of component receiving portion 119 to align and secure fluid pathway module 120 to base unit 110. FIG. 3A shows fluid pathway module 120 partially installed on base unit 110 and FIG. 3B shows fluid pathway module 120 fully installed on base unit 110.

In an exemplary embodiment, when fluid pathway module 120 is mounted to base unit 110, fluid pathway module 120 is positioned to receive gas from base unit 110. A gas outlet (not shown in FIGS. 2-4) of base unit 110 engages a gas inlet (not shown in FIGS. 2-4) of fluid pathway module 120 to form an airtight channel through which gas, received through inlet port 101a, may be transferred to fluid pathway module 120. As shown in FIGS. 2-4, fluid pathway module 120 is also configured to receive liquid from a liquid supply line 75 via liquid inlet 124. Liquid may be supplied to fluid pathway module 120, for example, via a sterile water bag (not shown) that is suspended above humidification system 100. The sterile water bag may be punctured by a tube spike (not shown), with water being gravity fed from the water bag into fluid pathway module 120 via liquid supply line 75. An exemplary tube spike is disclosed in U.S. patent application Ser. No. 10/918,515 owned by the Assignee of the present invention, which is incorporated herein in its entirety by reference. In an exemplary embodiment, liquid is stored within reservoir 32 (shown schematically in FIG. 1) in fluid pathway module 120 that is provided to receive humidification fluid from the water bag as well as recirculated humidification fluid. The circulated humidification fluid/liquid in fluid pathway module 120 liquid does not flow through base unit 110. Liquid contained in fluid pathway module 120 is vaporized in vapor transfer device 99 and combined with gas from base unit 110 to generate humidified breathing gas. As shown in FIG. 3A, a delivery tube 85 is releasably coupled to a breathing gas outlet 125 of fluid pathway module 120 to deliver humidified breathing gas to the patient.

As illustrated in FIG. 4, rear panel 102 of base unit 110 includes a pressure relief valve 91 that vents excess gas from base unit 110 if gas pressure supplied to base unit 110 from gas inlet ports 101a, 101b is too high. Base unit 110 also includes a service access cover 92 which is coupled to the rear panel 102 of base unit 110. Service access cover 92 may be removed from base unit 110 to provide access to internal components within base unit 110.

As shown in FIG. 4, an electrical cord 65 is coupled to base unit 110 to power humidification system 100. When electrical cord 65 is removed or AC power is temporarily unavailable, an internal battery (not shown) within base unit 110 may provide DC power to humidification system 100. Humidification system 100 may operate on DC power, for instance, when a patient is being transported from one location to another or during power interruptions, thus providing humidification system 100 portability and continued operations. In order to conserve battery power, the heater (not shown) that heats the fluid in fluid pathway module 120 does not operate in battery mode.

As further illustrated in FIG. 2, humidification system 100 has a front panel 104 that includes a display panel 105, such as a liquid crystal display (LCD) or light emitting diode (LED) display that provides visual indication of user settings and status conditions of humidification system 100. In an exemplary embodiment, the user settings may include user adjustable settings such as temperature 106a, flow rate 106b, and oxygen saturation level 106c of the breathing gas to be delivered to the patient. User settings may be adjusted, for example, via user interface 107. User interface 107 includes buttons 108a, 108b, LEDs 109a, 109b, and knob 111 to adjust and monitor operating conditions of humidification system 100. Additional aspects of the display panel 105 and user interface 107 will be described in further detail below according to aspects of humidification system 100 operation.

Figure 5:
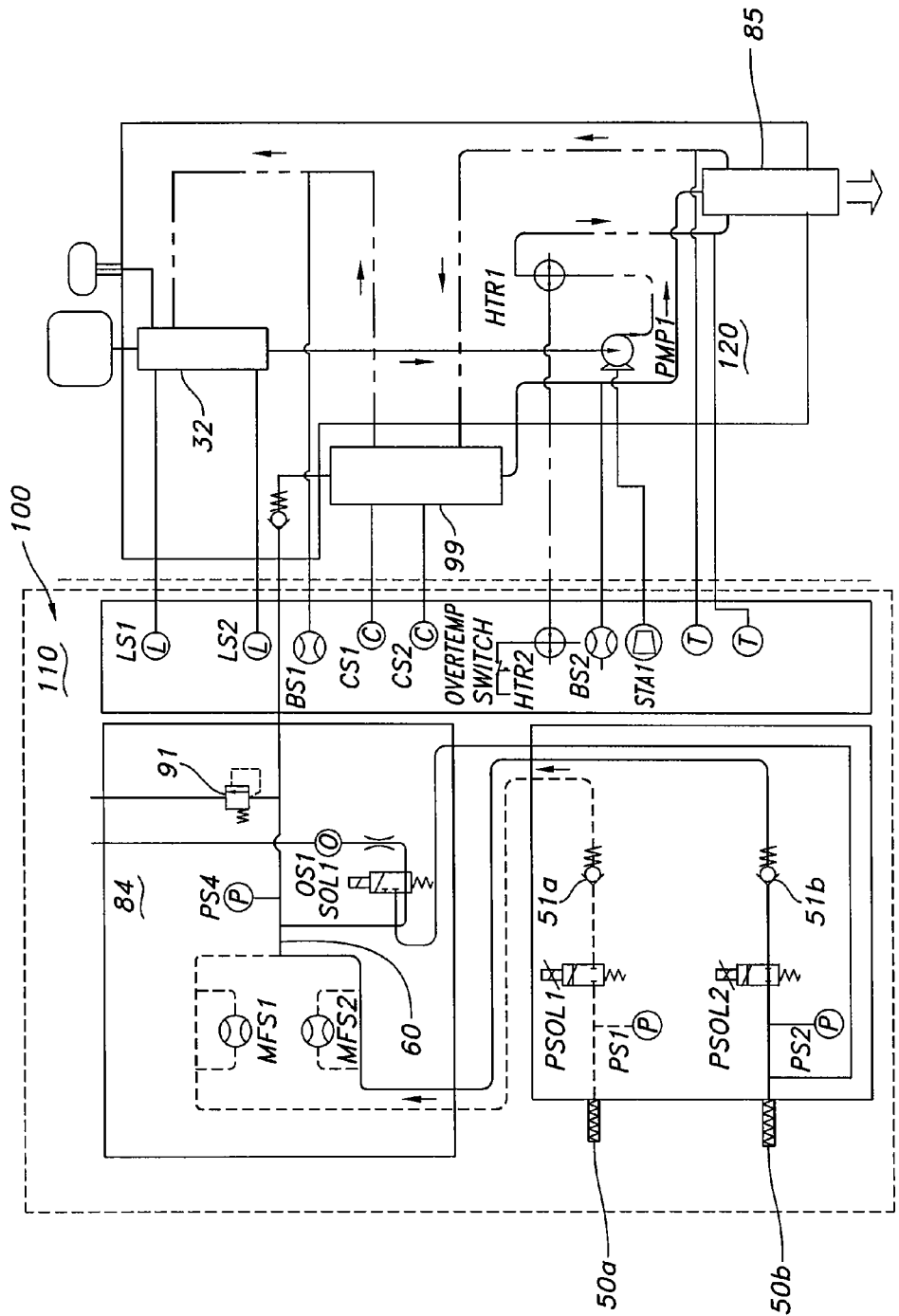
FIG. 5 is a schematic representation of the humidification system shown in FIGS. 2, 3, and 4 according to aspects of the invention.

Referring now to FIG. 5, a detailed schematic diagram of humidification system 100 showing gas and fluid flow paths is illustrated. Schematic representations of base unit 110, fluid pathway module 120, and vapor transfer device 99 are shown. Fluid pathway module 120 is configured to be releasably mounted to base unit 110, and vapor transfer device 99 is configured to be releasably mounted to fluid pathway module 120.

Base unit 110 includes controls for operation of humidification system 100 and has inlet ports configured to receive gas 50a, 50b, such as medical air and oxygen. Gas input into base unit 110 is controlled by two proportional solenoids PSOL1, PSOL2 that regulate the flow of gas 50a, 50b, respectively, into base unit 110. Proportional solenoids PSOL1, PSOL2, respectively, to regulate gas input flow into base unit 110. Gas pressure sensors PS1, PS2 monitor gas pressure upstream of solenoids PSOL1, PSOL2, respectively. Check valves 51a, 51b direct gas flow into gas blending device 84 and prevent reverse flow of gas 50a, 50b.

In an exemplary embodiment, gas flow rate of air 50a and oxygen gas 50b are monitored by mass flow sensor MFS1, MFS2, respectively, positioned on gas blending device 84. Air 50a and oxygen gas 50b are blended in gas blending device 84 and blended gas pressure is monitored by gas pressure sensor PS4. An oxygen sensor OS1 is coupled to a three-way solenoid valve SOL1 and monitors the oxygen saturation level of the blended gas. If the oxygen saturation level of the blended gas is below a user setpoint, proportional solenoid valve PSOL1 feeds additional oxygen gas 50b into the blended gas. Likewise, if oxygen saturation level of the blended gas is above a user setpoint, proportional solenoid valve PSOL1 reduces the amount of oxygen gas 50b into the blended gas. Gas pressure sensor PS4 is coupled to a microcontroller (not shown) and monitors the pressure of the blended gas. If the blended gas pressure exceeds a certain safety threshold, humidification system 100 emits an audible and a visual alarm. Additionally, when gas pressure sensor PS4 senses a low pressure, gas flow is limited by system 100.

As shown schematically in FIGS. 1 and 5, blended gas 60 is delivered to vapor transfer device 99, which is mounted to fluid pathway module 120. Sensors CS1, CS2 positioned within a base unit interface, such as component receiving portion 119, shown in FIG. 3, of base unit 110 detect the presence of vapor transfer device 99 coupled to fluid pathway module 120. For example, sensors CS1, CS2 may read a barcode or optically detect an indicator on vapor transfer device 99 when fluid pathway module 120 is mounted to base unit 110.

Fluid pathway module 120 receives water, e.g. from a water bag 33, into reservoir 32. Two water level sensors LS1, LS2 on base unit 110 monitor water level within reservoir 32. For example, water level may be monitored by optical detection, as will be described in further detail below. When fluid pathway module 120 is mounted to base unit 110, water from reservoir 32 is pumped by a pump portion PMP1 of fluid pathway module 120. Pump portion PMP1 is operationally coupled to a stator STA1 of base unit 110 to pump water from reservoir 32 to a heater HTR1. Heater HTR1 receives thermal energy from base unit heater HTR2 to heat water to a user specified temperature. A temperature switch (OVERTEMP SWITCH) controls heater HTR2 on base unit 110 to provide a safety backup to prevent water in fluid pathway module 120 from overheating. Heated water is pumped to a closed double lumen of a patient delivery tube 85 that is coupled to fluid pathway module 120. Heated water is recycled from delivery tube 85 into vapor transfer device 99. In an exemplary embodiment, heated water is supplied through patient delivery tube 85 to minimize water condensation of breathing gas 80 and to maintain the temperature of breathing gas 80 as it makes its way to the patient. Infrared temperature sensors (not shown) monitor the temperature of the water being delivered to and returned from delivery tube 85 and provide feedback to system controller (not shown) in order to maintain a desired temperature of the breathing gas at the outlet of delivery tube 85. Additional aspects of exemplary delivery tube 85 and vapor transfer device 99 are described in U.S. Patent Application Publication No. 2003/0209246 and U.S. Patent Application Publication No. 2004/0245658, which are incorporated herein fully by reference.

Blended gas from base unit 110 is combined with heated water vapor in vapor transfer device 99 to generate heated and humidified breathing gas 80. The heated and humidified breathing gas 80 is delivered to a breathing gas lumen of the patient delivery tube 85. Excess heated water delivered to vapor transfer device 99 may be recycled into water reservoir 32. Bubble sensor BS1 monitors air bubbles in reservoir 32 and bubble sensor BS2 monitors the presence of water droplets in the breathing gas 80 to determine when vapor transfer device 99 and/or fluid pathway module 120 should be replaced. In an exemplary embodiment, fluid pathway module 120 has a continuous duty life of about 720 hours and about a 1000 hour test life.

Gas Blending Device

Figure 6A:
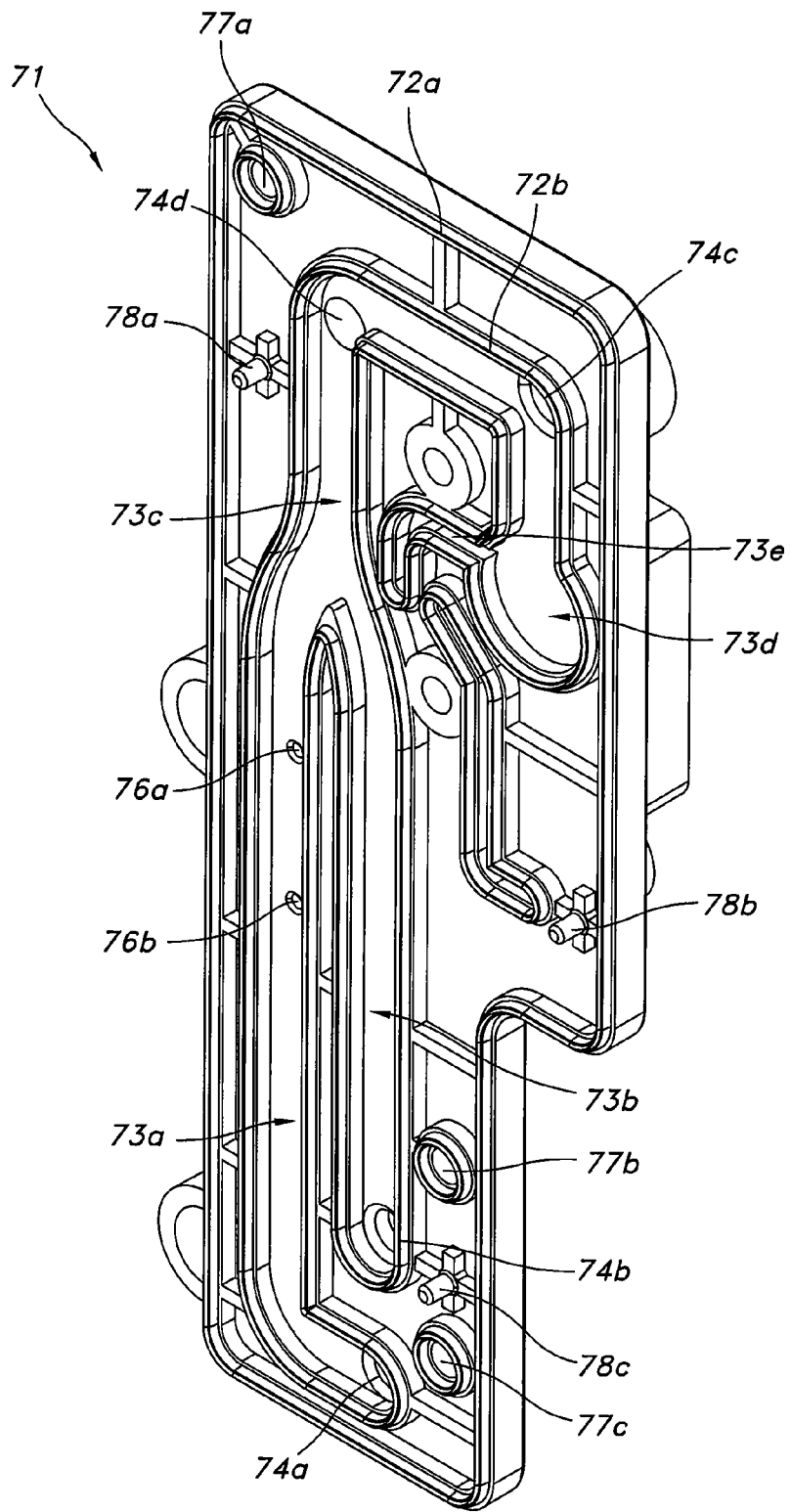
FIG. 6A is a perspective view of a first portion of a gas blending device according to an aspect of the invention.
Figure 6B:
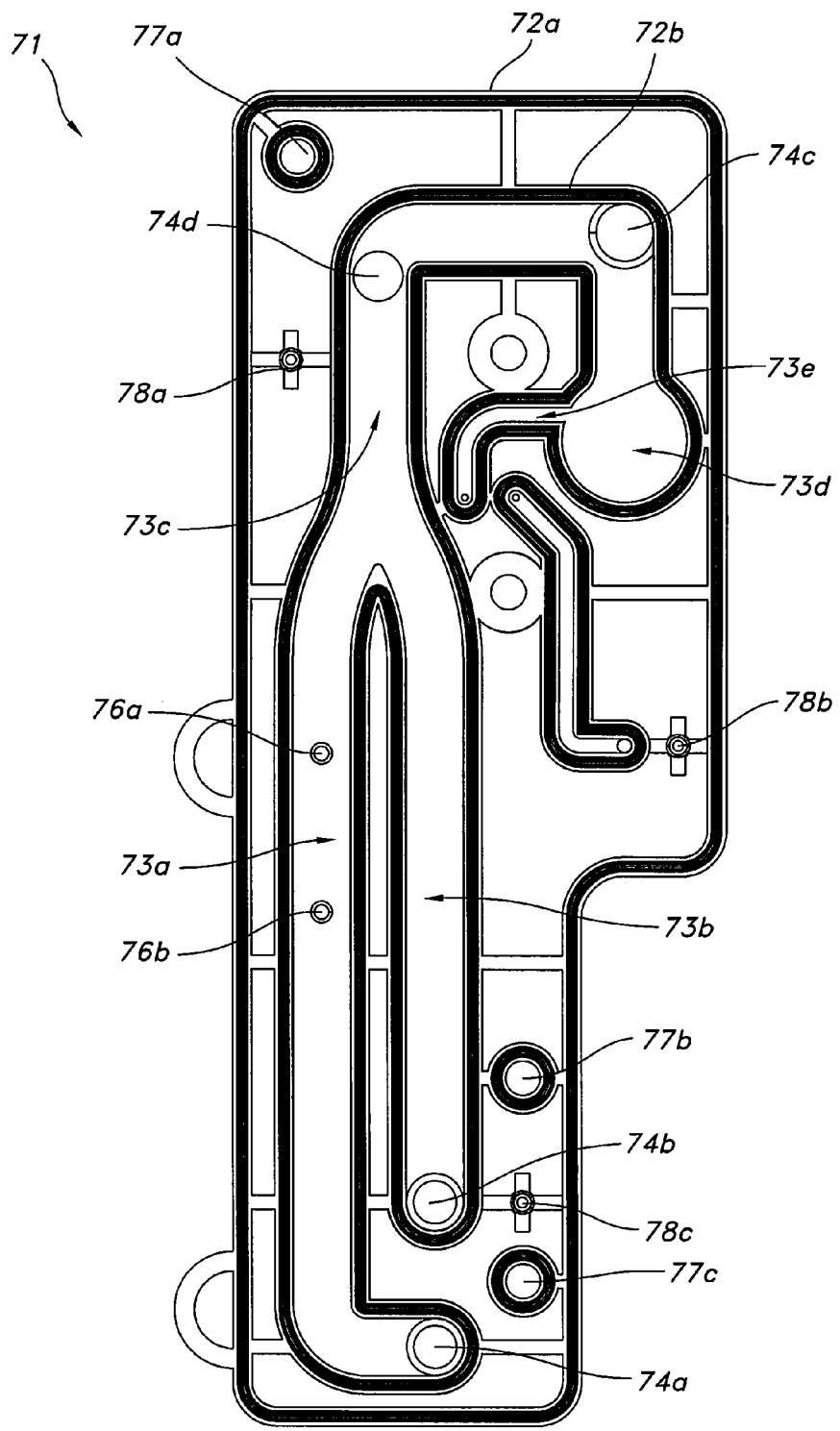
FIG. 6B is an interior view of the first portion of the gas blending device shown in FIG. 6A.
Figure 6C:
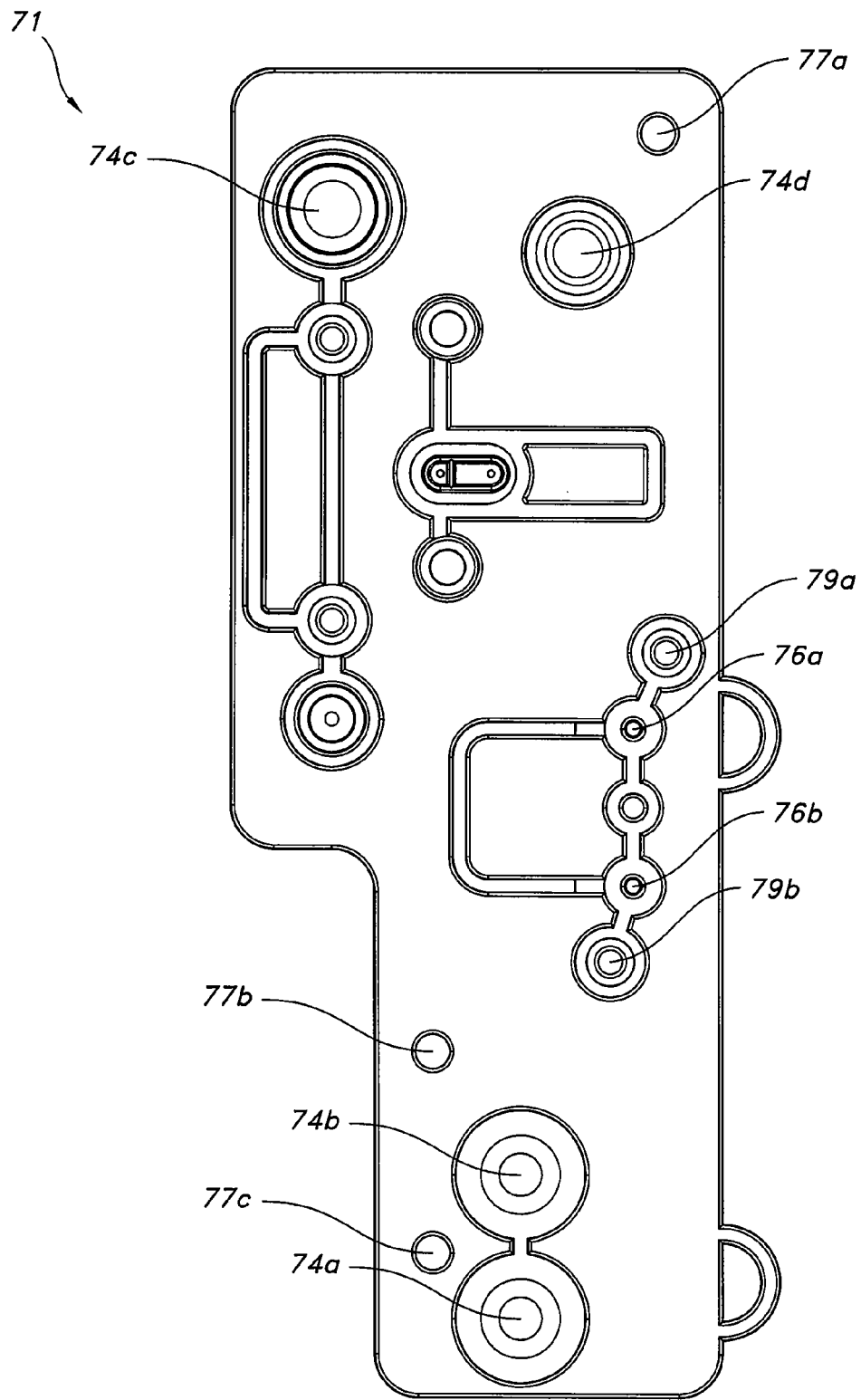
FIG. 6C is an exterior view of the first portion of the gas blending device shown in FIG. 6B.
Figure 7A:
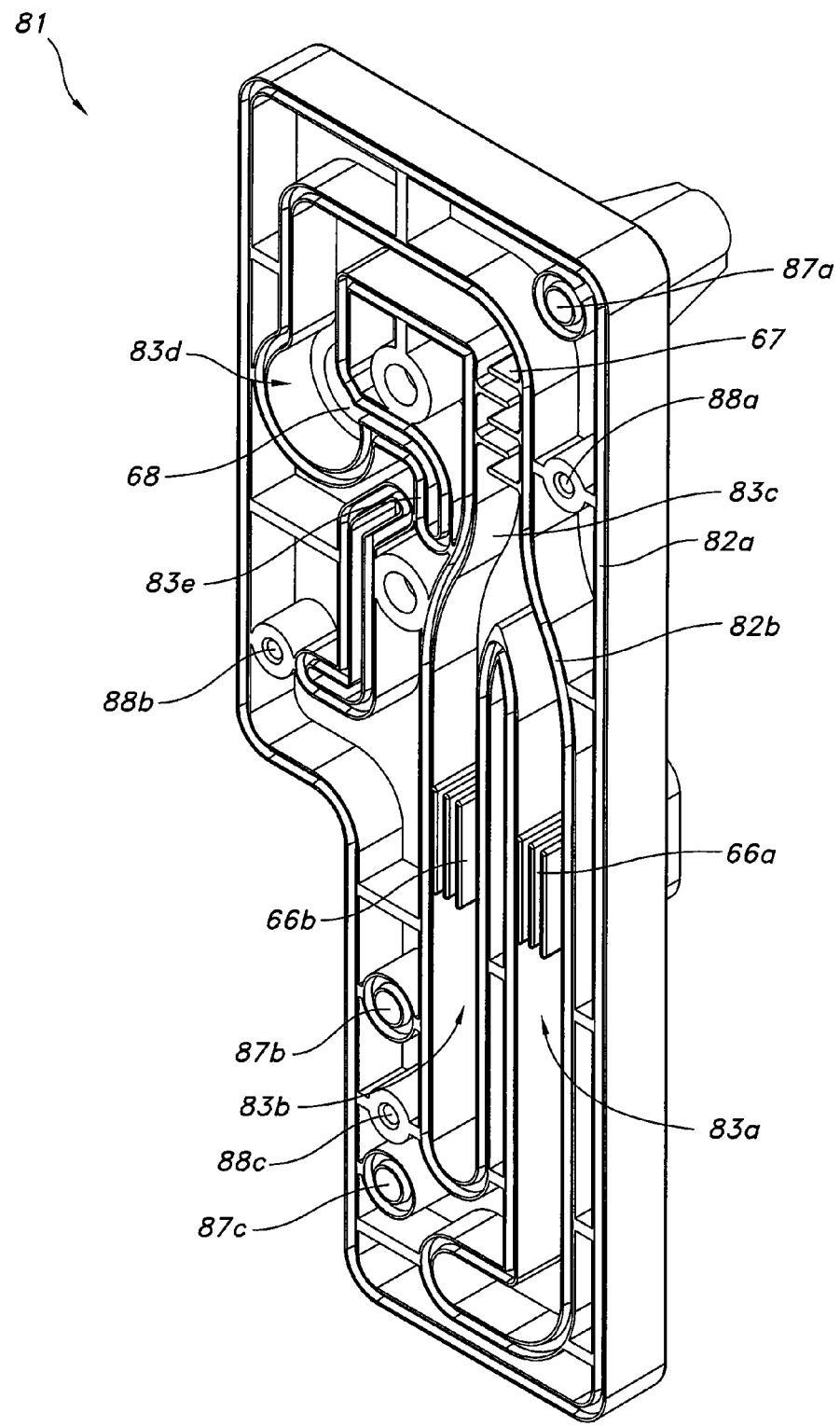
FIG. 7A is a perspective view of a second portion of the gas blending device configured to mate with the first portion shown in FIG. 6A.
Figure 7B:
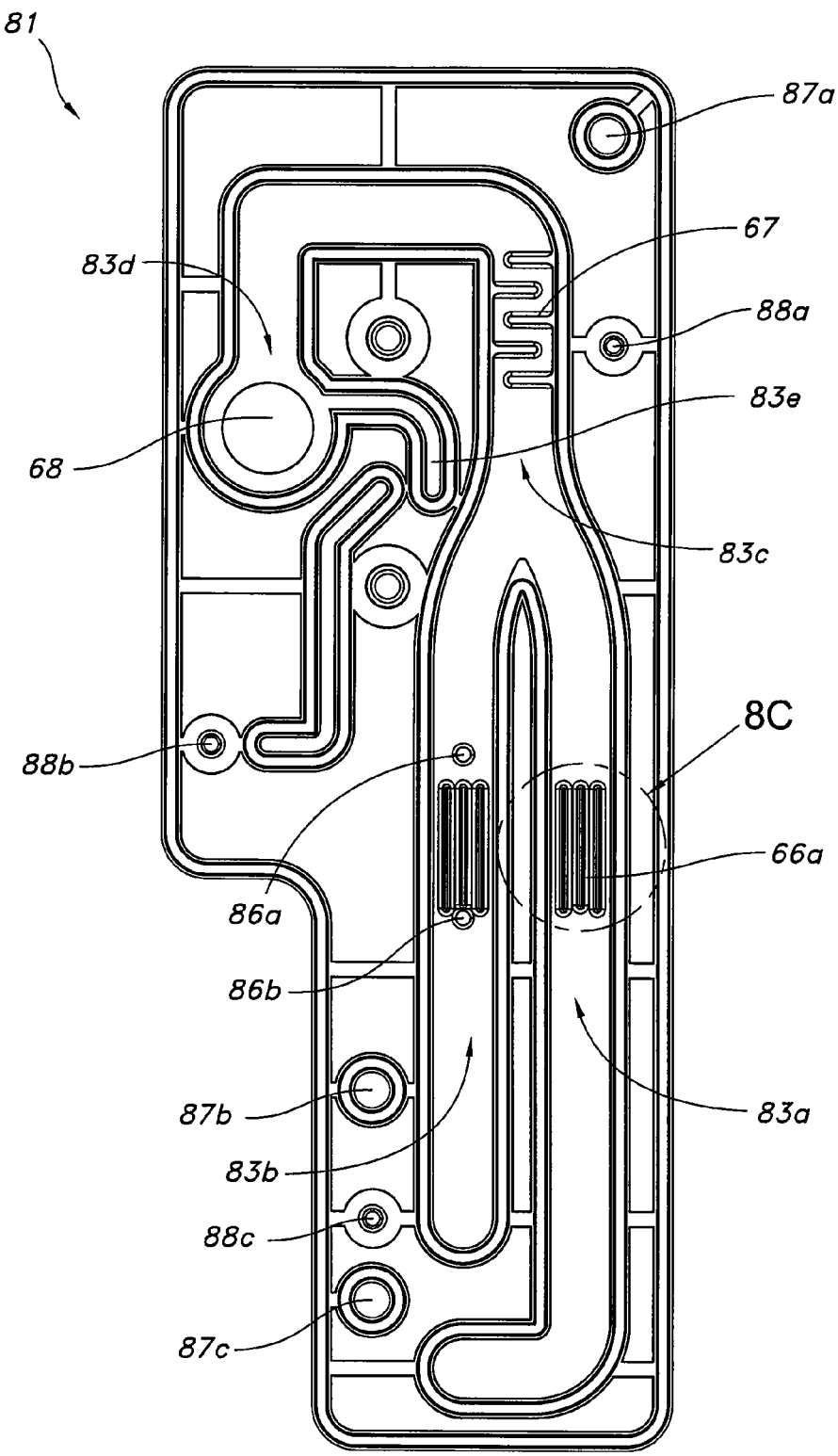
FIG. 7B is an interior view of the second portion of the gas blending device shown in FIG. 7A.
Figure 7C:
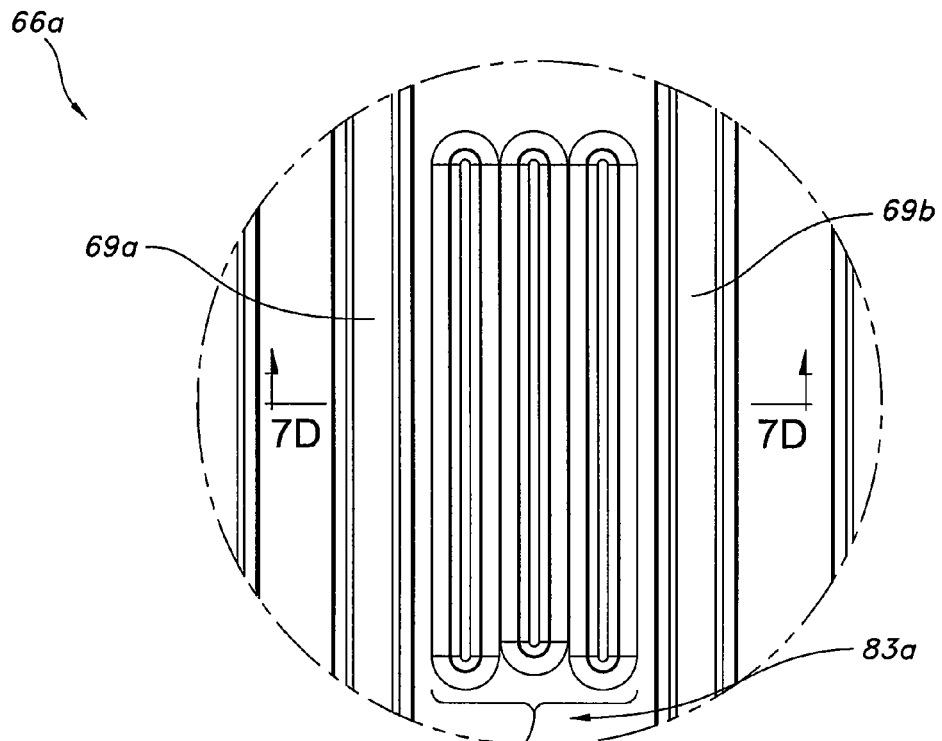
FIG. 7C is an enlarged view of laminar fins shown in FIG. 7B.
Figure 7D:
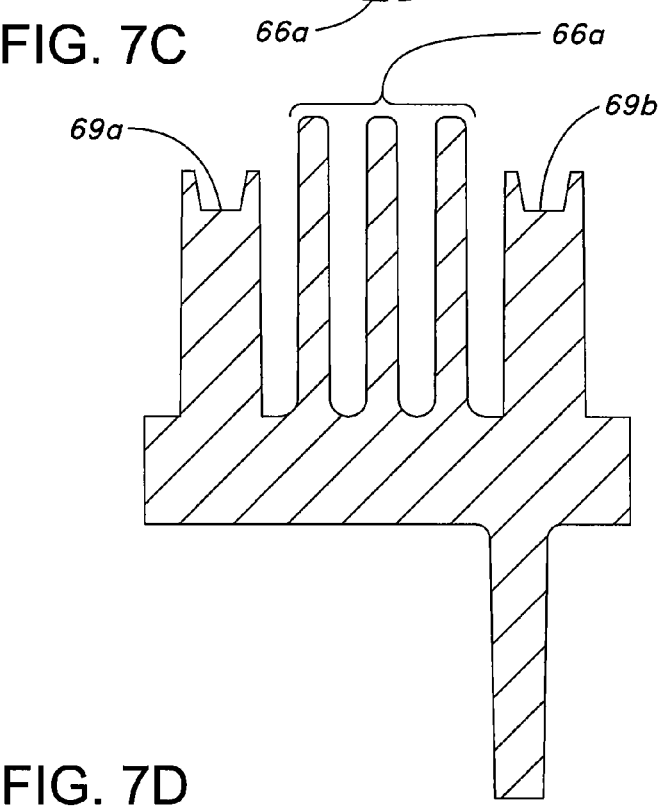
FIG. 7D is a cross-sectional view of the laminar fins, taken along lines 7D-7D of FIG. 7C.

Referring now to FIGS. 6A, 6B, 6C, 7A and 7B, gas blending device 84 is illustrated. Reference to these figures also includes references to sensors represented in FIG. 5. Gas blending device 84 may be constructed from a first, generally planar portion 71 (FIGS. 6A, 6B, 6C) and a second generally planar portion 81 (FIGS. 7A, 7B). Planar portions 71, 81 each include complementary channels such that when planar portions 71, 81 are assembled together, flow passages are formed within gas blending device 84. For example, channels 73a and 83a combine to form a first passage, channels 73b and 83b combine to form a second passage, and channels 73c and 73c combine to form a third passage. First portion 71 is configured to mate with second portion 81 shown in FIGS. 7A-7B to provide a fully assembled gas blending device 84. When first portion 71 is secured to second opposing portion 81, edges 72a, 72b of first portion 71 form an air tight seal with edges 82a, 82b of second portion 81 to prevent gas leakage and provide efficient gas blending operation. Gas blending device 84 is configured to be installed internally within base unit 110.

Pilot holes 77a-c and pins 78a-c, shown in FIGS. 6A-6C, are positioned on first portion 71 of gas blending device 84 to align and secure the first portion 71 to the second opposing portion 81 shown in FIGS. 7A-7B. In an exemplary embodiment, pilot holes 77a-c and pins 78a-c provide additional connection surface area and mechanical strength to the gas blending device 84. Pilot holes 87a-c and pin inserts 88a-c are positioned on the body of second portion 81 and are configured to mate with pilot holes 77a-c and pins 78a-c of the first portion 71.

An interior view of the first portion 71 of gas blending device 84 is illustrated in FIGS. 6A and 6B. First portion 71 of gas blending device 84 includes two channels 73a, 73b that are each configured to receive gas through inlets 74a, 74b, respectively. Channels 73a, 73b direct gas to blending channel 73c. Blending channel 73c leads to main terminal channel 73d where blended gas may exit through second portion 81 and flow to a gas outlet, shown as gas outlet 649 in FIG. 8C, of base unit 110. Upstream of main terminal channel 73d is a pressure relief outlet 74c that functions as a secondary gas exit if gas pressure exceeds a predetermined value. In an exemplary embodiment, pressure relief outlet 74c is part of a pressure relief valve system, which may open or close pressure relief valve 91 (shown schematically in FIG. 5), depending on gas pressure within gas blending device 84. Passage 73e provides for gas flow to oxygen sensor OS1 (shown schematically in FIG. 5).

Referring now to FIGS. 7A and 7B an interior view of second portion 81 of gas blending device 84 is shown. Second portion 81 of gas blending device 84 is configured to mate with the first portion 71 shown in FIGS. 6A-6C. Second portion 81 includes channels 83a, 83b having fins 66a, 66b within each channel 83a, 83b. Fins 66a, 66b promote laminar flow across mass flow sensors MFS1, MFS2 (shown schematically in FIG. 5) installed through openings 76a, 76b of the first portion 71 (FIG. 7B) of gas blending device 84. Walls 69a, 69b define channel 83a such that when gas blending portion 71 (FIG. 6B) mates with the second opposing portion 81 (FIG. 7B), air tight channels are formed.

Channels 83a, 83b direct gas to a blending channel 83c that includes a tortuous path 67 to efficiently mix gas together prior to reaching terminal channel 83d. Channel 83e mates with channel 73e to form a passage to oxygen sensor OS1 (shown schematically in FIG. 5).

In an exemplary embodiment, gas metering operation of humidification system 100 determines the precise flow rate of gas within each channel 73a, 83a to obtain a blended gas mixture having an oxygen saturation level between 21% and 100% $O_2$. Oxygen saturation level of blended gas mixture 60 shown in FIG. 1 may be monitored by oxygen sensor OS1, which is shown in FIG. 5.

As shown in FIGS. 6A-6C, first portion 71 of gas blending device 84 includes sensor openings 76a, 76b which open into either end of passage 76c. Passage 76c is in fluid communication with mass flow sensor MFS1 (not shown in FIGS. 6A-6C), which monitors gas flow rate in channel 73a to control the gas metering operation of humidification system 100. FIG. 6C illustrates an exterior view of first portion 71 of gas blending device 84. First portion 71 includes threaded inserts 79a, 79b to mount mass flow sensor MFS1.

Figure 7E:
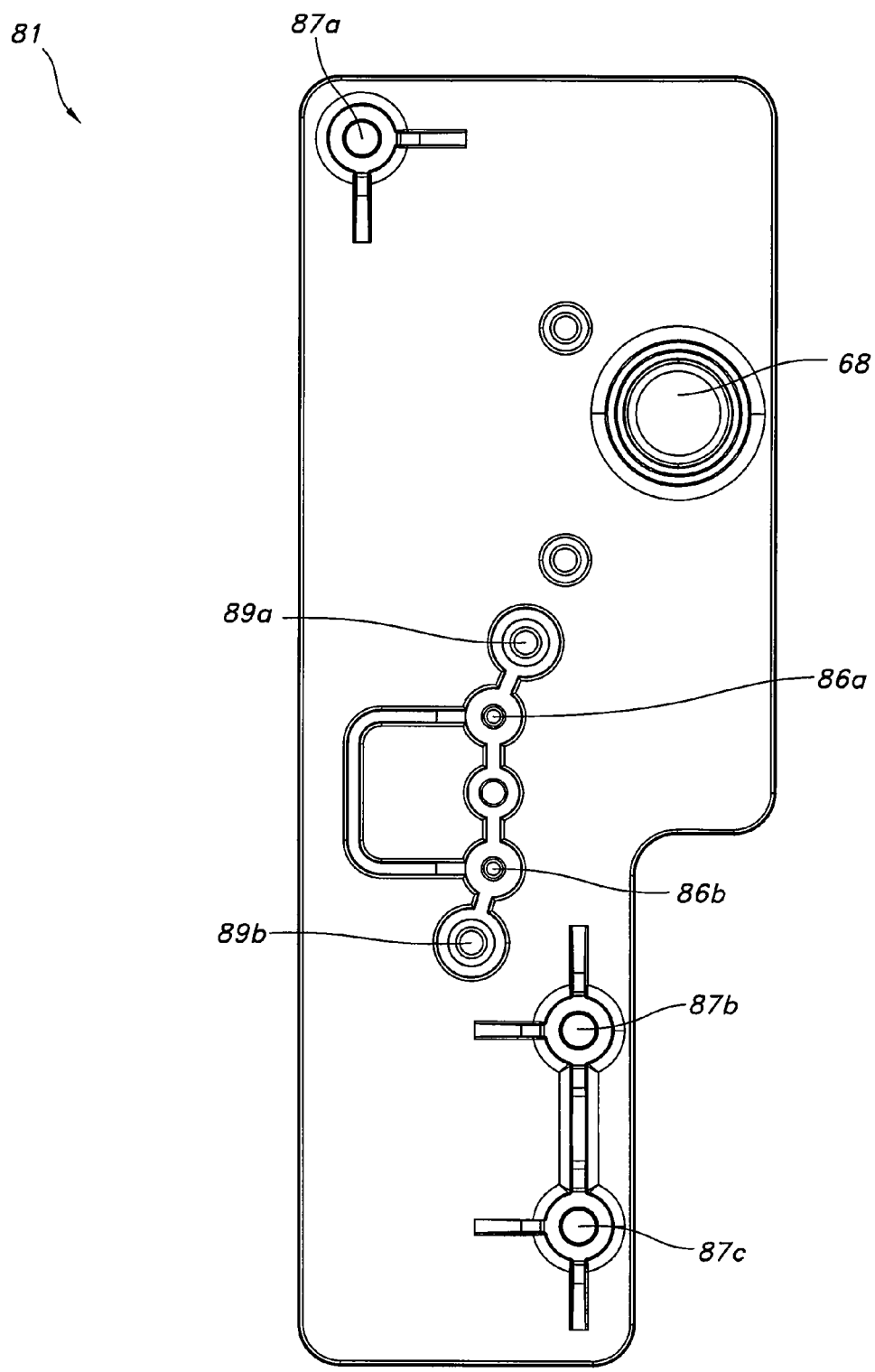
FIG. 7E is an exterior view of the second portion of the gas blending device shown in FIG. 7B.

As shown in FIG. 7B, channel 83b of second portion 81 includes sensor openings 86a, 86b which open into either end of passage 86c. Passage 86c is in fluid communication with mass flow sensor MFS2 (not shown in FIGS. 7A-7B), which monitors gas flow rate in channel 83a to control the gas metering operation of humidification system 100. FIG. 7E illustrates an exterior view of second portion 81 of gas blending device 84. Second portion 81 includes threaded inserts 89a, 89b to mount mass flow sensor MFS2 through openings 86a, 86b. Main gas outlet 68 provides an exit for blended gas to flow to gas outlet 649, shown in FIG. 8C, of base unit 110.

The gas flow rate detected by mass flow sensor MFS1, MFS2 in channel 73a may be sent to a microcontroller that controls proportional solenoid valves PSOL1, PSOL2. Proportional solenoid valve PSOL1 or PSOL2 may vary gas input flow in channel 73a by increasing or decreasing gas flow through the inlet 74a. Thus, an adequate ratio of gas flow may be supplied to channel 73a to obtain a desired blended oxygen saturation level. In an exemplary embodiment, oxygen sensor OS1, which may be positioned in oxygen sensor opening 74d, is calibrated to 100% $O_2$ during a system power up sequence. Once calibrated, the oxygen sensor OS1 measures oxygen content of blended gas to ensure that blended gas is within 98% to 102% of a selected oxygen percentage setpoint. If detected oxygen content falls below 98% of the selected oxygen level, the microcontroller may adjust proportional solenoid valves PSOL1, PSOL2 to increase the flow of oxygen gas 50b and/or decrease the flow of air 50a. Alternatively, if detected oxygen content is above 102% of the selected oxygen level, the microcontroller may adjust proportional solenoid valves PSOL1, PSOL2 to decrease the flow of oxygen gas 50b and/or increase the flow of air 50a through inlet 74b or 74a.

Base Unit Chassis

Referring now to FIGS. 8A-8G, an exemplary embodiment of a base unit chassis 640 is illustrated. Base unit chassis 640 contains the interfaces with fluid pathway module 120. References to these figures also include references to sensors BS1, BS2, electronic readers CS1, CS2, water level sensors LS1, LS2, temperature sensors IR1, IR2, pump stator STA1, and heater HTR2, which are shown schematically in FIG. 5 and with reference to base unit 110 in FIG. 8G. It will be appreciated that base unit chassis 640 houses the electronic components of humidification system 100 and is configured such that liquid does not flow internally through base unit 110.

Figure 8A:
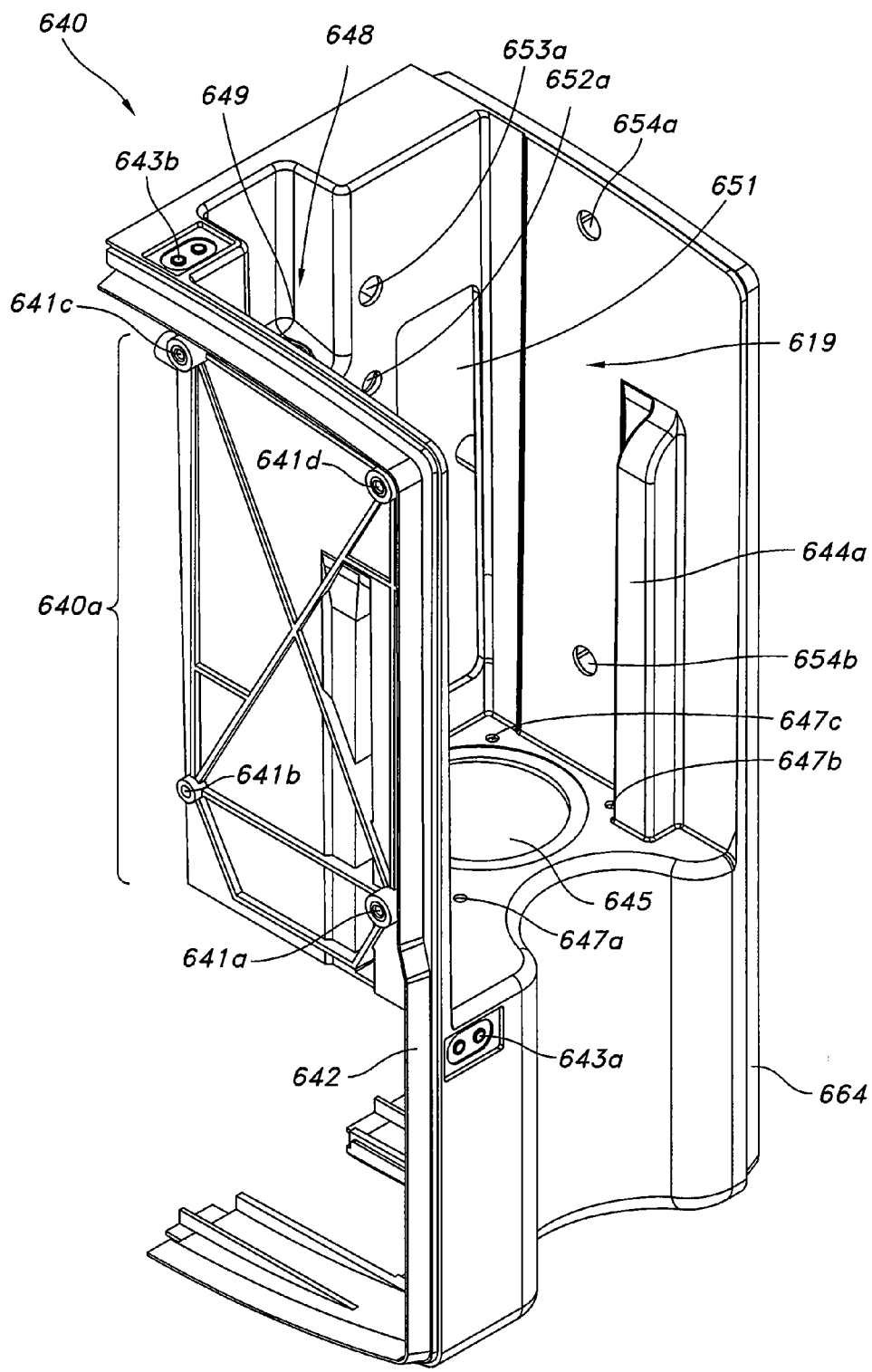
FIG. 8A is a front perspective view of a chassis of the humidification system.

As shown in FIGS. 2 and 8A, base unit chassis 640 includes a front portion 640a into which display panel 105 may be installed. Threaded inserts 641a-d are provided on front portion 640a of chassis 640 to secure display panel 105 to base unit chassis 640. When display panel 105 is secured, front panel 104 may be fitted over a front edge 642 of base unit chassis 640 to prevent access to the electrical connections of display panel 105. After installation of front panel 104, slidable door 103 as shown in FIG. 3, may be secured to base unit chassis 640 via threaded inserts 643a, 643b located on the top and side of base unit chassis 640.

As shown in FIGS. 3A, 3B, and 8A, base unit chassis 640 includes a component receiving portion 619 configured to receive fluid pathway module 120. A guide 644a extends along the side of the component receiving portion 619 to align and secure fluid pathway module 120 to base unit 100. Base unit chassis 640 has a seat 645 to support fluid pathway module 120 and a seat opening 646 in which a pump portion such as stator STA1 may be installed via threaded inserts 647a-c. When fluid pathway module 120 is seated in component receiving portion 619, stator STA1 (shown schematically in FIG. 5) of base unit 110 operationally mates with pump portion PMP1 (shown schematically in FIG. 5) of fluid pathway module 120. In an exemplary embodiment, stator STA1 may drive pump portion PMP1 which may be an impeller that is magnetically driven by stator STA1 to advance liquid through a liquid passage of fluid pathway module 120. An exemplary embodiment of a pump having a separate pump portion PMP1 and a separate stator portion STA1 is manufactured by Laing Thermotech, Inc., located in Chula Vista, Calif. In yet another embodiment (not shown), the entire pump portion may be provided only on base unit 110 to provide a low cost, disposable fluid pathway module 120. Alternatively, the entire pump portion may be provided only on fluid pathway module 120

Base unit chassis 640 includes a recessed portion 648 that has a gas outlet 649. When fluid pathway module 120 is inserted on base unit 110, recessed portion 648 aligns with and supports a gas receiving portion 130, shown in FIG. 10B, of fluid pathway module 120. The gas receiving portion of fluid pathway module 120 includes a gas inlet which is configured to couple to the gas outlet 649 of base unit 110 to provide an air tight seal through which gas may be transferred from base unit 110 to the gas passage of fluid pathway module 120.

The component receiving portion 619 of base unit chassis 640 has a rectangular opening 651 into which heater HTR2, shown in FIG. 5, such as a heat conduction plate may be installed. When fluid pathway module 120 is releasably mounted to base unit 110, heater HTR2 of base unit 110 contacts heater HTR1, FIG. 5, of fluid pathway module 120, FIG. 3. Heater HTR1 of fluid pathway module 120 may also be a heat conduction plate HTR2 such that when electrical current is supplied to the heat conduction plate of base unit 110, energy is transferred to heat conduction plate HTR1 of fluid pathway module 120. Thermal energy received by heat conduction plate HTR1 of fluid pathway module 120 is used to heat the liquid contained within fluid pathway module 120 for delivery to the patient at a temperature specified by the user. In an exemplary embodiment, the user may adjust the temperature setting of humidification system in 1° C. steps to a maximum temperature of 43° C. and a minimum temperature of 33° C. A temperature sensor opening 652a in base unit chassis 640 is configured to receive temperature sensor IR1 to monitor the temperature of the liquid that is supplied to delivery tube 85.

Base unit chassis 640 also includes a bubble sensor opening 653a adjacent temperature sensor opening 652a. Bubble sensor opening 653a is configured to receive bubble sensor BS1 that monitors the formation of air bubbles in liquid reservoir 32 of fluid pathway module. Additional aspects of bubble sensor BS1 will be described in further detail below.

Referring to FIGS. 5 and 8A, two water level sensor openings 654a, 654b are positioned on base unit chassis 640. Water level sensor openings 654a, 654b are each configured to receive a water level sensor LS1, LS2 to monitor the water level within liquid reservoir 32 of fluid pathway module 120. In an exemplary embodiment, optical water level sensors LS1, LS2 are aimed at reflectors 128a, 128b, shown in FIG. 10A, located at the top and bottom of liquid reservoir 32 to determine when the liquid reservoir 32 is full, low, or empty. Additional aspects of water level sensors LS1, LS2, shown in FIG. 5, will be described in further detail below.

Figure 8B:
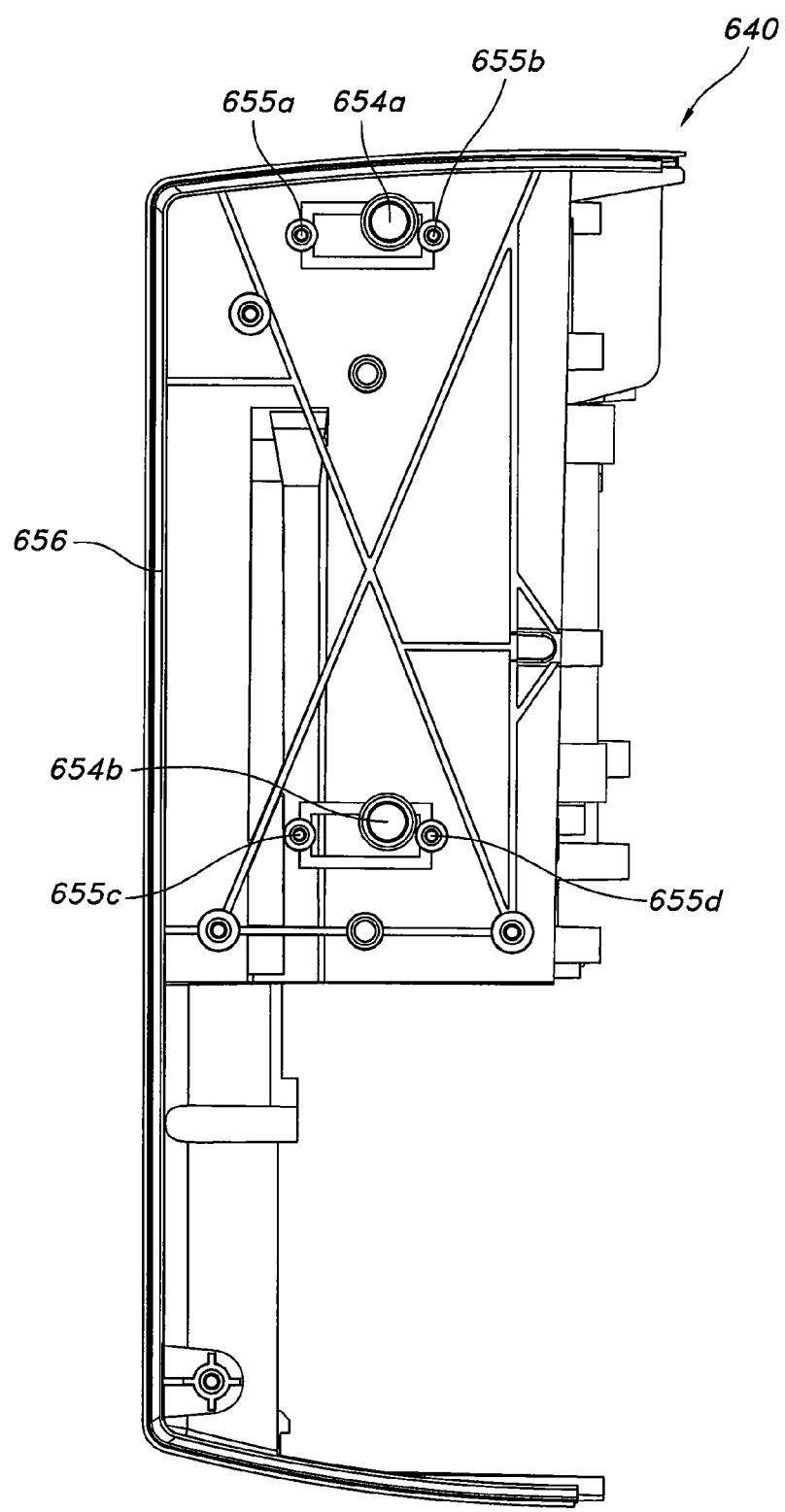
FIG. 8B is a rear elevation view of the chassis shown in FIG. 8A.

FIG. 8B illustrates a rear view of base unit chassis 640 in which water level sensors LS1, LS2 may be installed. As described above, water level sensor openings 654a, 654b are each configured to receive a water level sensor LS1, LS2, respectively. Water level sensors LS1, LS2 may be mounted to base unit chassis 640 via threaded inserts 655a-d. Rear panel 102, shown in FIG. 4, may be fitted over rear edge 656 of base unit chassis 640 to restrict access to the electrical connections of water level sensors LS1, LS2.

Figure 8C:
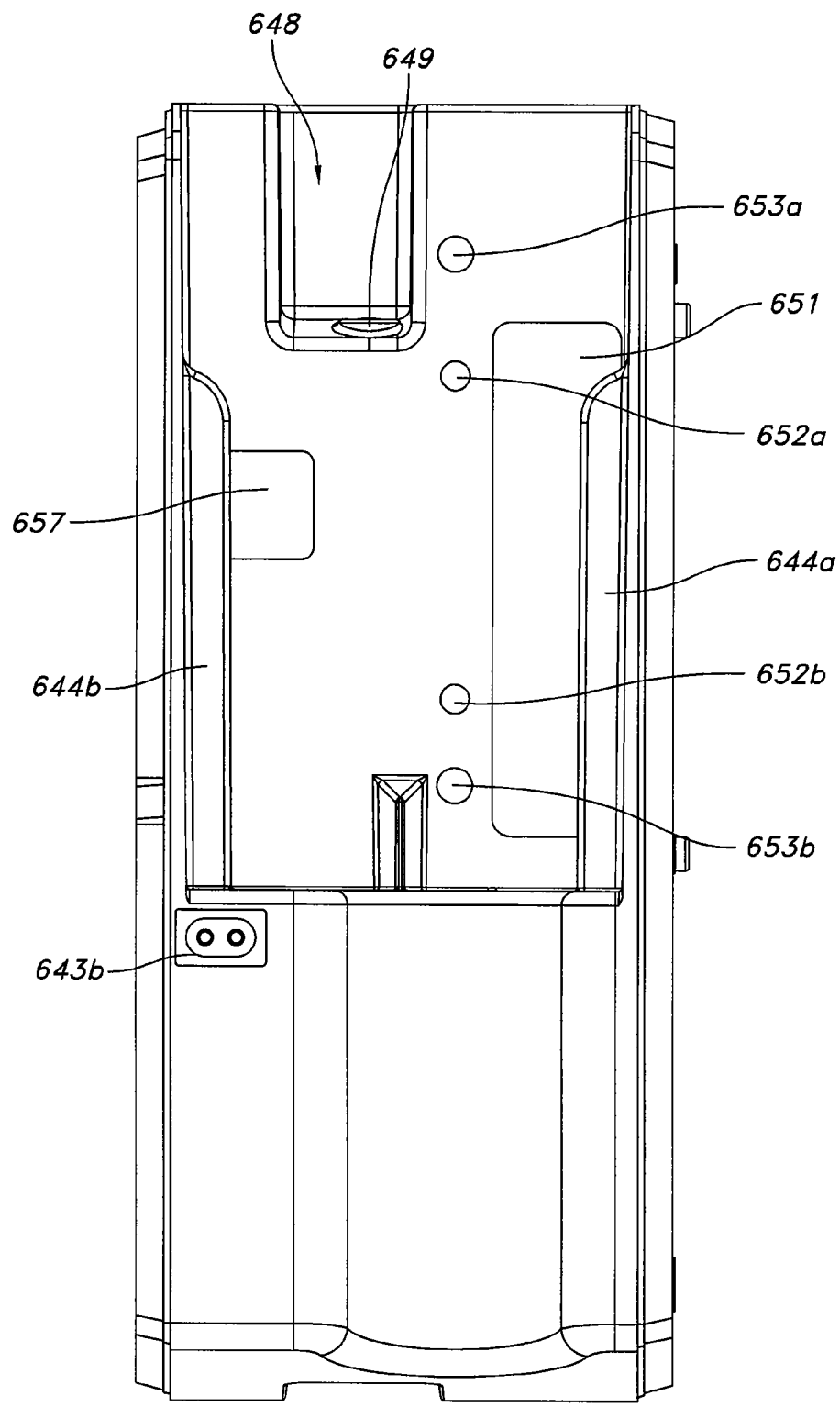
FIG. 8C is an exterior side elevation view of the chassis shown in FIG. 8A.

FIG. 8C illustrates a side view of base unit chassis 640 in which fluid pathway module 120, shown in FIG. 3, may be releasably mounted. An electronic reader opening 657 on base unit chassis 640 is configured to receive electronic reader CS1, CS2 that detects the type of vapor transfer device 99 coupled to fluid pathway module 120. Vapor transfer device 99 may be, for example, a disposable, cartridge that is labeled with an indicator 194 such as a sticker or barcode. In an exemplary embodiment, a high flow vapor transfer device 99 is labeled with an all-reflective sticker while a low flow vapor transfer device 99 is labeled with a portion reflective/portion non-reflective sticker. Electronic reader CS1, CS2 may monitor the optical properties of the sticker to identify the type of vapor transfer device 99 installed in humidification system 100. When indicator 194 is read by electronic reader CS1, CS2, a signal is sent to a microprocessor (not shown) to control the gas metering operation of humidification system 100. For example, when a low flow rate vapor transfer device 99 is installed, the microcontroller may limit the flow rate of the breathing gas being delivered to a setpoint between 0.5 LPM (liters per minute) and 8 LPM. If a high flow rate vapor transfer device 99 is installed, the microcontroller may limit the flow rate between 8 LPM and 40 LPM. In an exemplary embodiment, when a user attempts to adjust the flow rate setpoint beyond the limits defined by the microcontroller, humidification system 100 generates an auditory warning and prevents the setpoint from deviating beyond the maximum and minimum flow rate limits of a high flow or low flow vapor transfer device 99.

Referring to FIGS. 5 and 8C, a temperature sensor opening 652a of base unit chassis 640 is configured to receive infrared temperature sensor IR1 that detects the temperature of liquid in fluid pathway module 120. A second temperature sensor opening 652b is configured to receive second infrared temperature sensor IR2 that detects the temperature of liquid returning back to fluid pathway module 120 from delivery tube 85. In an exemplary embodiment, monitoring of the two temperatures allows humidification system 100 to efficiently operate heater HTR2, which is mounted through heater opening 651 of base unit chassis 640. For example, activation and deactivation of HTR2 may be controlled by a PID (proportional-integral-derivative) feedback controller to maintain a consistent temperature of the breathing gas being delivered to a patient.

Adjacent the temperature sensor openings 652a, 652b of base unit chassis 640 are bubble sensor openings 653a, 653b that are each configured to receive a bubble sensor BS1, BS2, respectively. During operation of humidification system, air bubbles may be detected in liquid reservoir 32 of fluid pathway module 120 due to air permeating under pressure through the exchange media in vapor transfer device 99 of fluid pathway module 120. Under normal operating conditions, the water and gas passages of fluid pathway module 120 are connected to vapor transfer device where a portion of the liquid is transferred to the gas. Over time, as gas and liquid flow internally through vapor transfer device, the core of vapor transfer device may begin to degrade such that the mixing interface between the gas and liquid passages erodes. As the interface degrades, gas from the gas passage may pass into the liquid passage such that air bubbles begin to form in liquid reservoir 32 of fluid pathway module 120. Conversely, liquid from the liquid passage may pass into the gas passage such that liquid droplets are mixed into the gas flow. Bubble sensors BS1, BS2 that are mounted in bubble sensor openings 653a, 653b of base unit chassis 640 detect these conditions and send appropriate signals to the microcontroller to warn a user of when either or both conditions exist.

In an exemplary embodiment, bubble sensor BS1, shown in FIG. 5, of humidification system 100 detects the rate at which air bubbles are formed in liquid reservoir 32 of fluid pathway module 120. If the bubble formation rate rises above a predetermined level, an auditory warning may be generated and vapor transfer device fault icon 112c, shown in FIG. 13, may illuminate on display panel 105 to indicate that vapor transfer device 99 should be replaced with a new cartridge. Alternatively, second bubble sensor BS2 detects the rate at which liquid droplets form in the gas passage of vapor transfer device 99. If the droplet formation rate exceeds a predetermined level, the gas metering and warming operations of humidification system 100 may be suspended. An auditory warning may be generated and fluid pathway module 120 icon 115, shown in FIG. 13, may illuminate on display panel 105, shown in FIG. 13, to indicate that fluid pathway module 120 should be replaced.

Figure 8D:
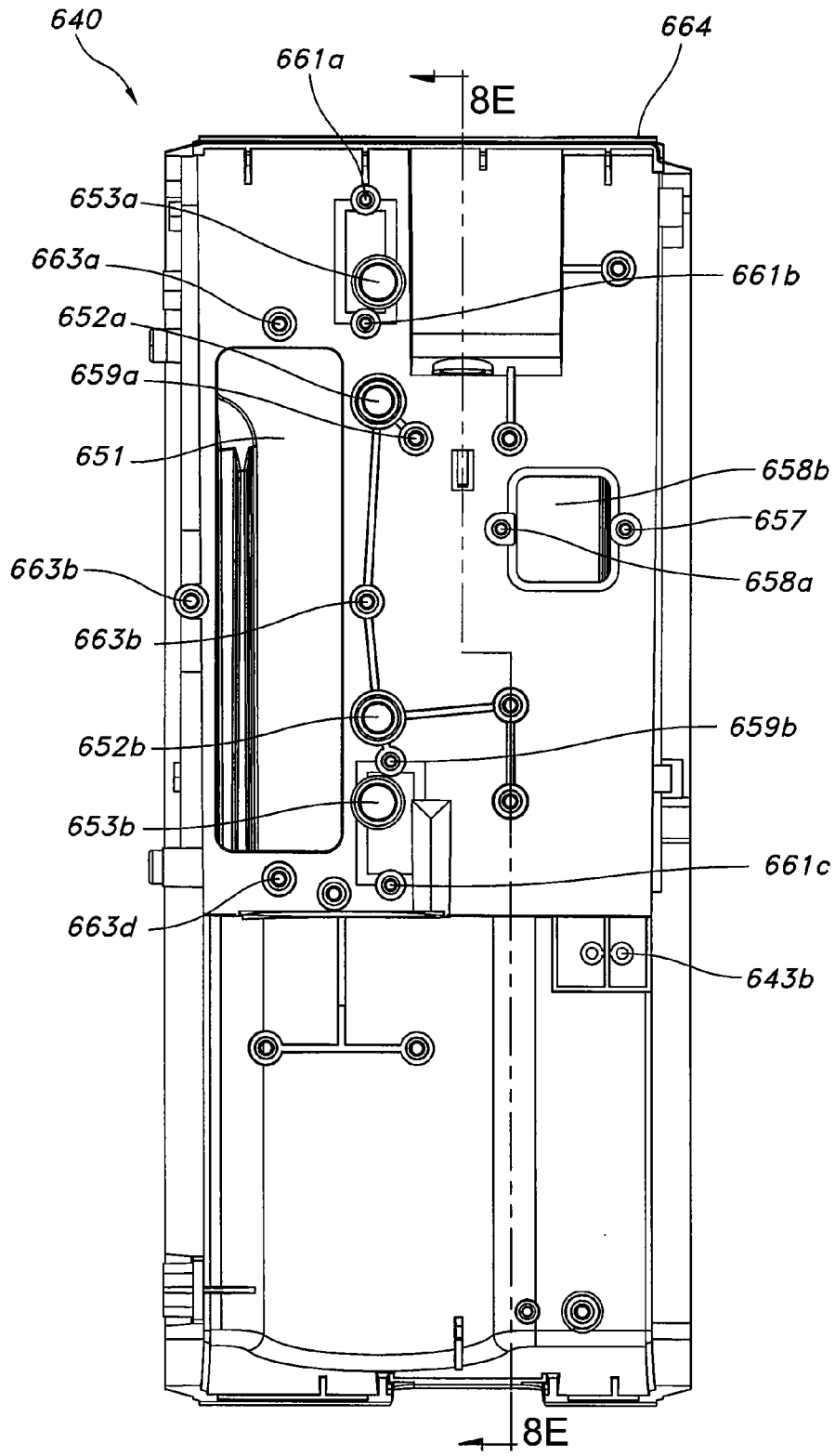
FIG. 8D is an interior side elevation view of the chassis shown in FIG. 8C.

FIG. 8D illustrates a side view of base unit chassis 640 in which electronic reader CS1, CS2, temperatures sensors IR1, IR2, bubble sensors BS1, BS2, and heater HTR2 may be installed. As described above, electronic reader opening 657 is configured to receive electronic reader CS1, CS2 which may be installed on base unit chassis 640 via threaded inserts 658a, 658b. Temperature sensor openings 652a, 652b are each configured to receive temperature sensor IR1, IR2, which may be mounted to base unit chassis 640 via threaded inserts 659a, 659b and bubble sensors BS1, BS2 may be mounted to bubble sensor openings 653a, 653b via threaded inserts 661a-c. Heater HTR2 such as a heat conduction plate may be mounted to the heat conduction plate opening 651 via threaded inserts 663a-d. A side panel (not shown) may be fitted over the rear edge 664 of base unit chassis 640 to restrict access to the electrical connections of electronic components, such as readers CS1, CS2, bubble sensors BS1, BS2 (FIG. 5), temperature sensors IR1, IR2, and heater HTR1, which are all shown schematically in FIG. 5.

Figure 8E:
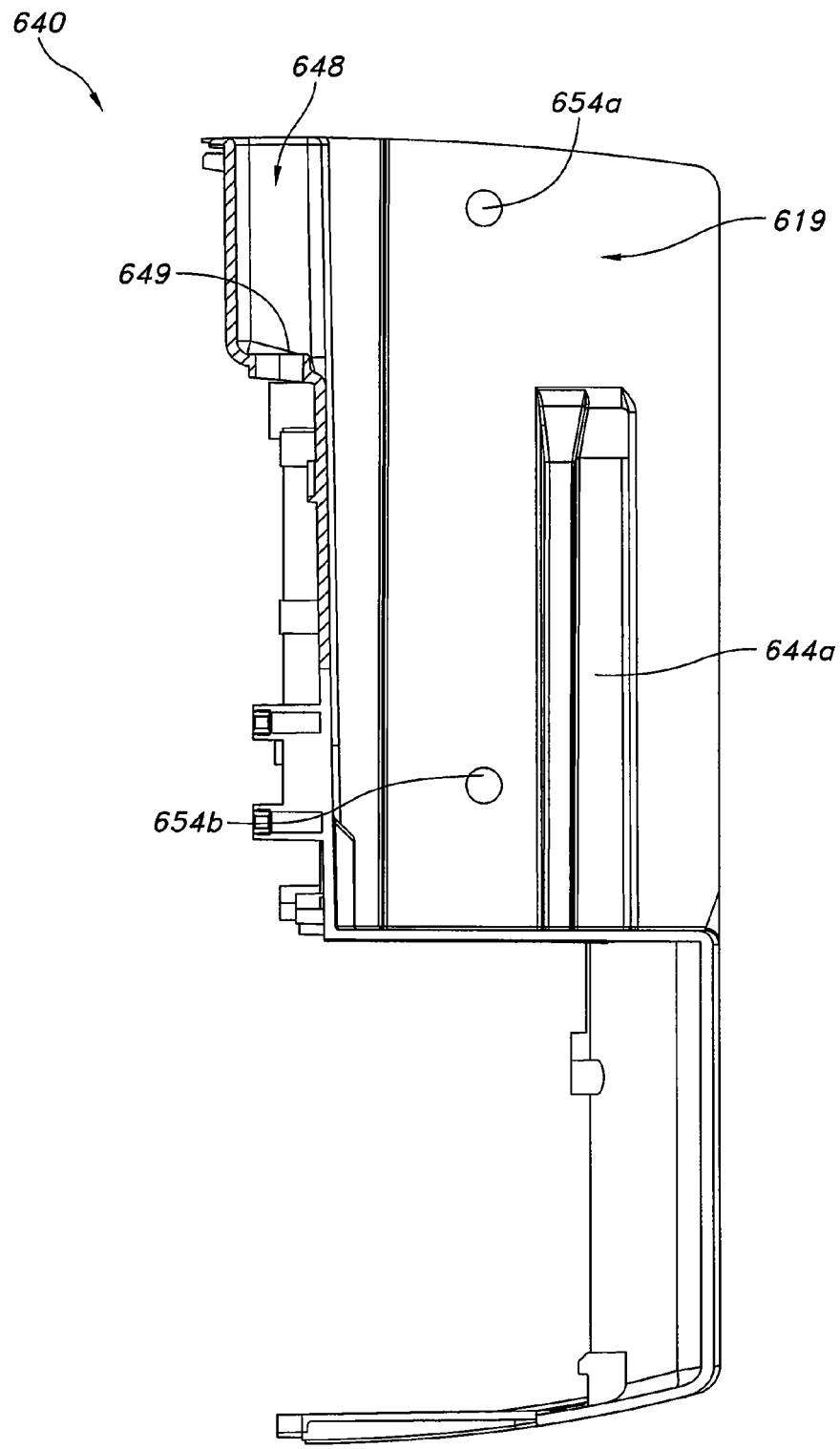
FIG. 8E is a cross-sectional view of the chassis, taken along lines 8E-8E of FIG. 8D.

FIG. 8E illustrates a cross-sectional view of base unit chassis 640 along the 8E-8E line shown in FIG. 8D. As shown in FIG. 8E, base unit chassis 640 includes a recessed portion 648 configured to receive a gas receiving portion of fluid pathway module 120. Gas outlet 649 of recessed portion 648 is configured to receive a gas inlet of fluid pathway module 120 to supply gas into the gas passage of fluid pathway module 120. Water level sensor openings 654a, 654b are disposed along the top and bottom of the component receiving portion 619 and are configured to receive water level sensors LS1, LS2 to detect water level in fluid pathway module 120. Guide 644a extends from the side of the component receiving portion 619 to align and secure fluid pathway module 120 to base unit 110.

Figure 8F:
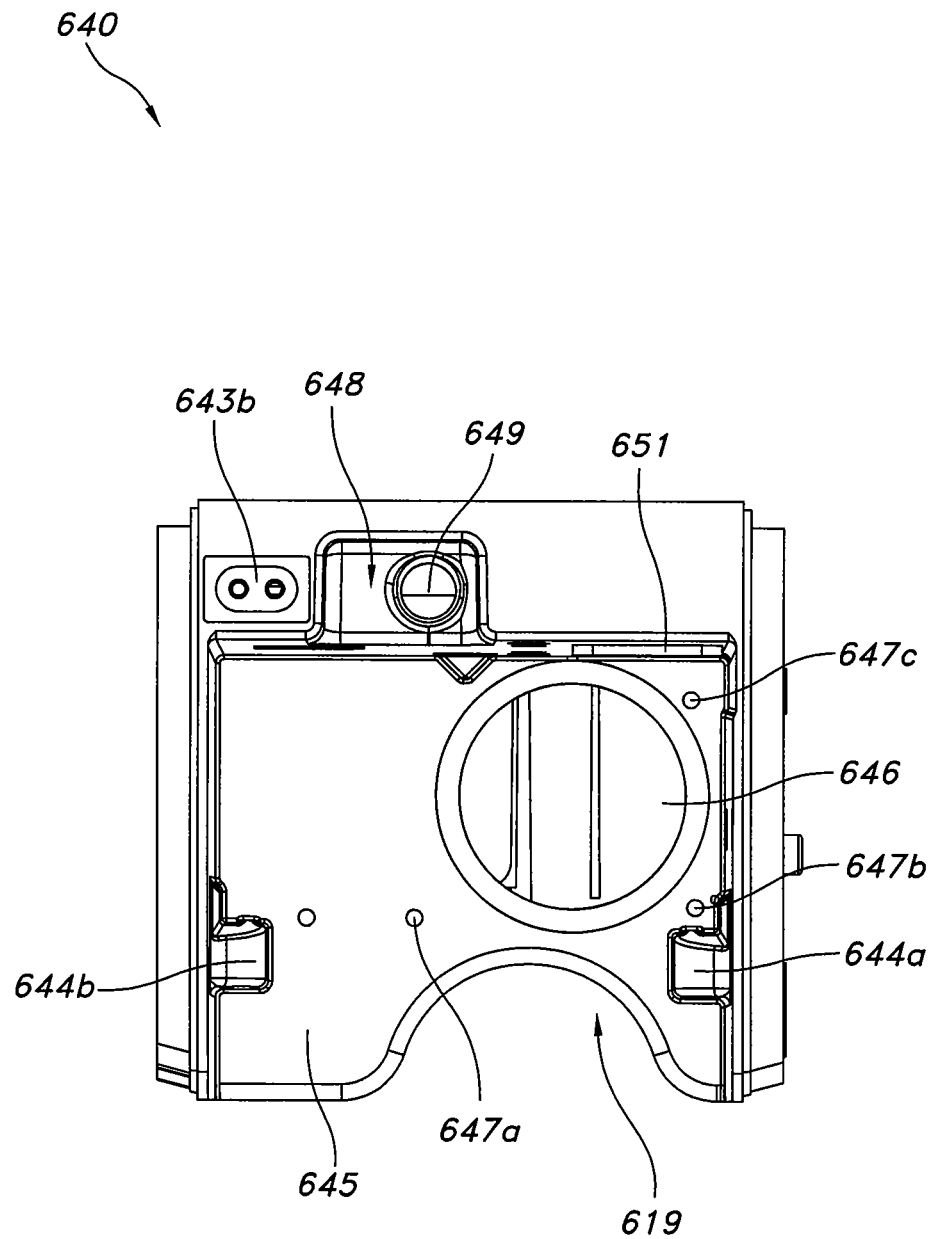
FIG. 8F is a top view of the chassis shown in FIG. 8A.
Figure 8G:
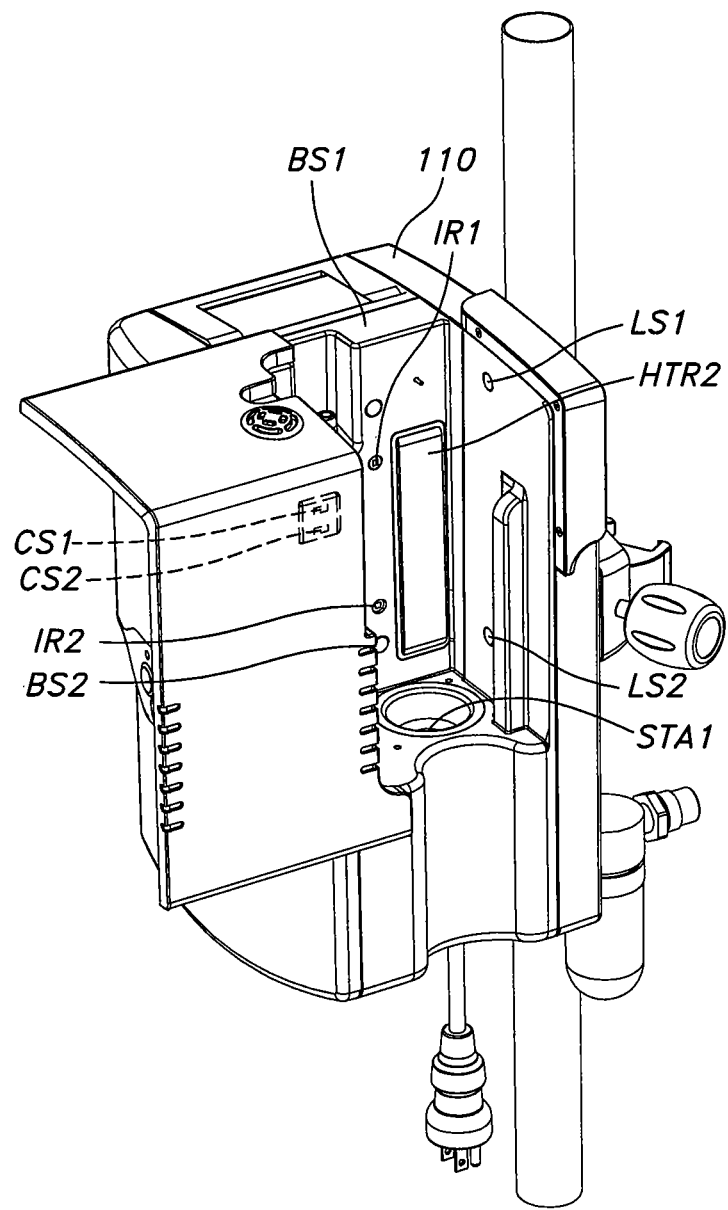
FIG. 8G is a top perspective view of an exemplary base unit that may be used with the chassis of FIG. 8A.

FIG. 8F illustrates a top view of base unit chassis 640. As described above, base unit chassis 640 includes a component receiving portion 619 having a seat 645 that is configured to seat fluid pathway module 120. A seat opening 646 is provided to receive pump portion STA1 of base unit 110 which may be secured to base unit 110 via threaded inserts 647a-c. Guides 644a, 644b extend from the side of the component receiving portion 619 to align and secure fluid pathway module 120 to base unit 110. A recessed portion 648 of base unit chassis 640 includes a gas outlet 649 which receives gas inlet of fluid pathway module 120. Opening 651 is positioned on base unit chassis 640 to receive heater HTR2.

Figure 9:
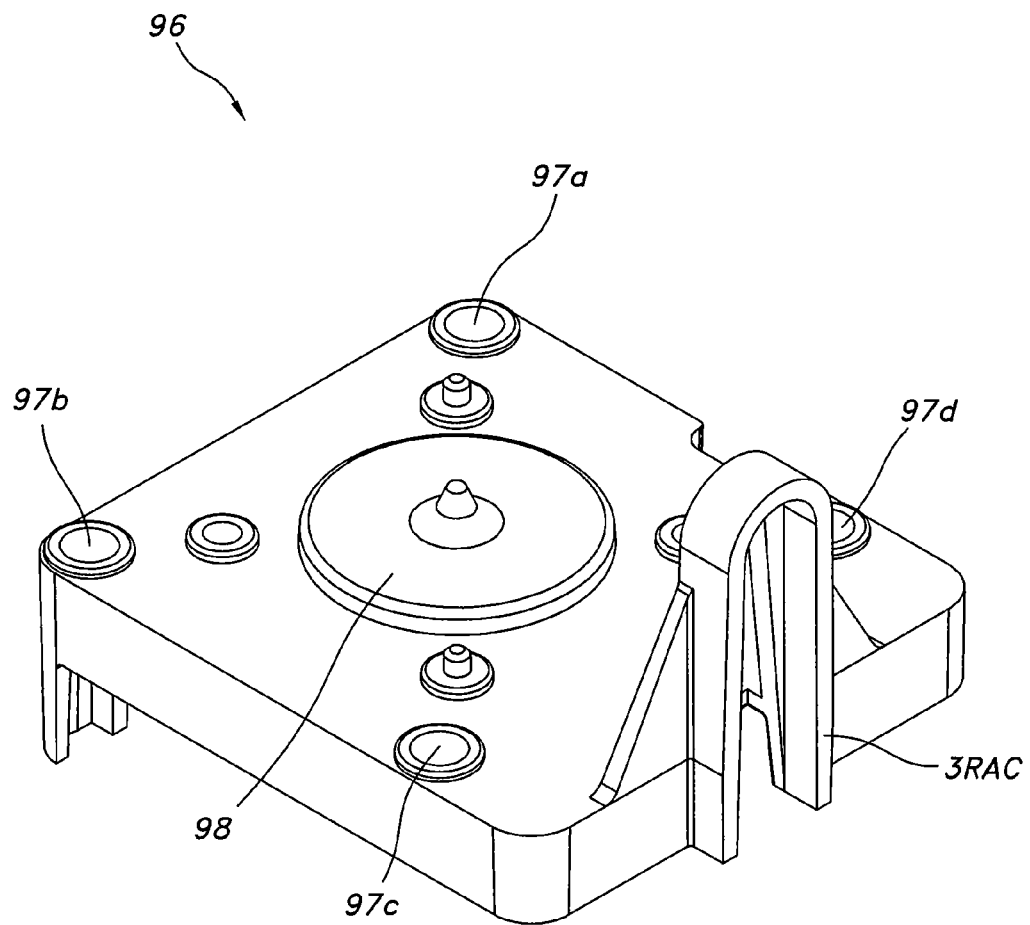
FIG. 9 is a perspective view of a pump portion the humidification system according to an aspect of the invention.

Referring now to FIG. 9, a pump portion 96 of base unit 110 is illustrated. Pump portion 96 is configured to mount to seat opening 646, shown in FIG. 8A, of base unit chassis 640 via openings 97a-d on pump portion 96. Installation bracket 99 facilitates alignment and installation of pump portion 96 Pump portion 96, such as stator STA1 shown in FIG. 5, is configured to operationally mate with pump portion PMP1 of fluid pathway module 120 to advance liquid through the liquid passage of fluid pathway module 120. In an exemplary embodiment, pump portion PMP1 of fluid pathway module 120 is a rotatable impeller 98 that magnetically couples to pump portion 96. When impeller 98 is operationally mated with pump portion 96, rotation of impeller 98 drives the rotation of pump portion PMP1, thereby increasing pressure and liquid flow within fluid pathway module 120.

Fluid Pathway Module (Vapor Transfer Unit)

Referring now to FIGS. 3A, 3B, 10A and 10B, an exemplary embodiment of fluid pathway module 120 shown in FIG. 3 is illustrated. Fluid pathway module 120 is configured to be releasably mounted to base unit 110 to accommodate reuse of base unit 110 and selective disposal of fluid pathway module 120.

Figure 10A:
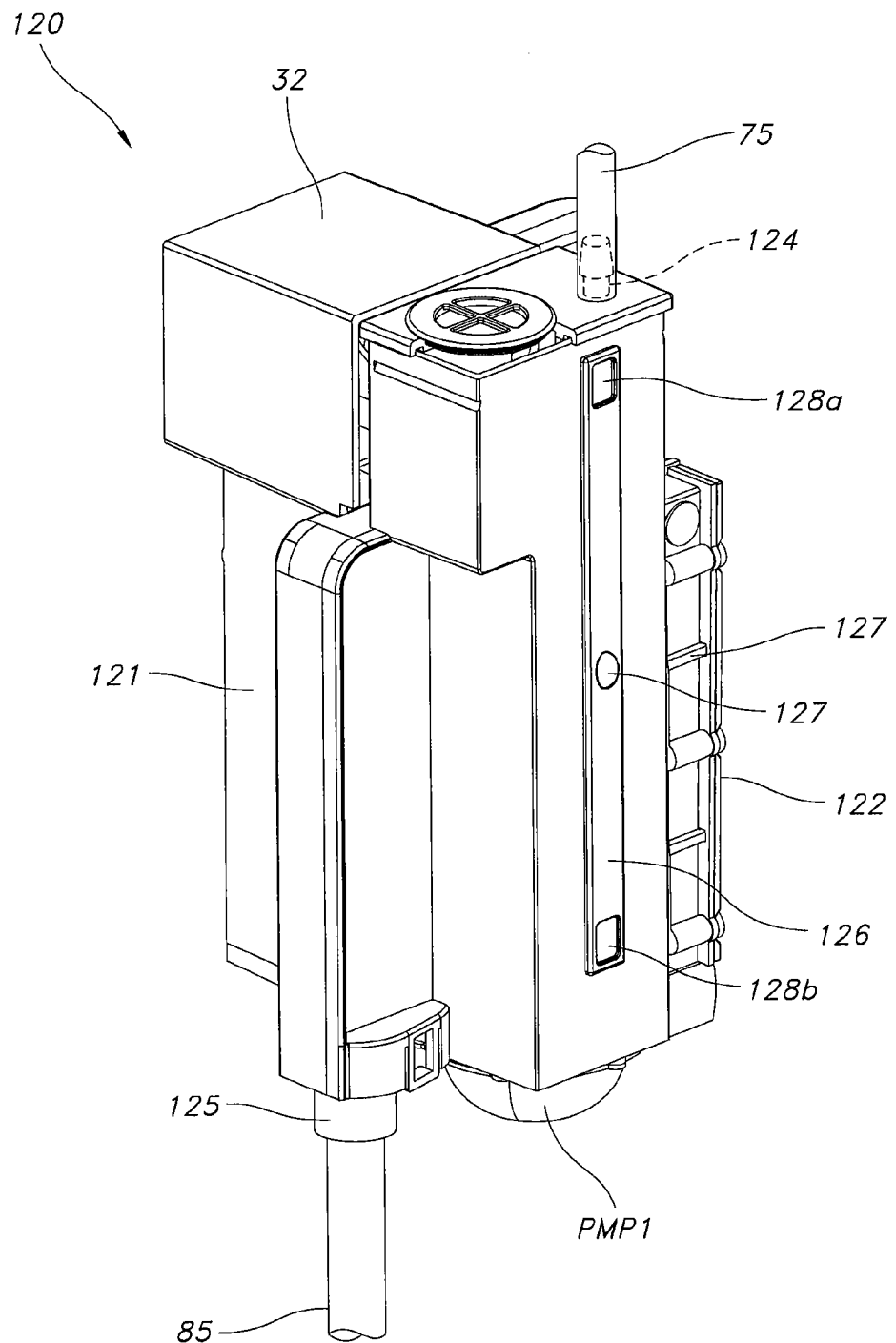
FIG. 10A is front perspective view of a fluid pathway module of the humidification system shown in FIG. 3.

Referring to FIGS. 3A, 5, and 10A, features and sensors of fluid pathway module 120 are discussed. Fluid pathway module 120 includes handle 121 that may be used to insert and remove fluid pathway module 120 from base unit 110. When fluid pathway module 120 is mounted to base unit 110, heater HTR1 contacts heater HTR2. Pump portion STA1 of base unit 110 engages pump portion PMP1 of fluid pathway module 120. As shown in FIG. 10A, fluid pathway module 120 includes liquid inlet 124 and gas outlet 125. Liquid inlet 124 receives liquid from supply line 75 and gas outlet 125 delivers heated and humidified breathing gas to a patient via delivery tube 85.

When liquid (such as water) is supplied to liquid inlet 124, liquid is stored within reservoir 32 of fluid pathway module 120. A sight glass 126 on the side of fluid pathway module 120 provides visual indication of liquid amount in reservoir 32 via a plastic ball 127 floating within reservoir 32. Two reflectors 128*a*, 128*b* are visible through the sight glass 126 and are positioned to align with water level sensors LS1, LS2. Water level sensors LS1, LS2 of base unit 110 optically sense water level in fluid pathway module 120 by monitoring light reflection off reflectors 128*a*, 128*b*. For example, when reservoir 32 is full, light reflection from reflector 128*a* is blocked by plastic ball 127 and the humidification system microcontroller (not shown) determines that water level in fluid pathway module 120 is full. When reservoir 32 is empty, light reflection from reflector 128*b* is blocked by plastic ball 127 and humidification system 100 may cease operation until water is added. If light is reflected from both reflectors 128*a*, 128*b*, plastic ball 127 is floating between reflectors 128*a*, 128*b* and microcontroller (not shown) may illuminate a low water icon 116, shown in FIG. 13, on display panel 105, shown in FIG. 3, of base unit 110 to indicate a low water condition.

Figure 10B:
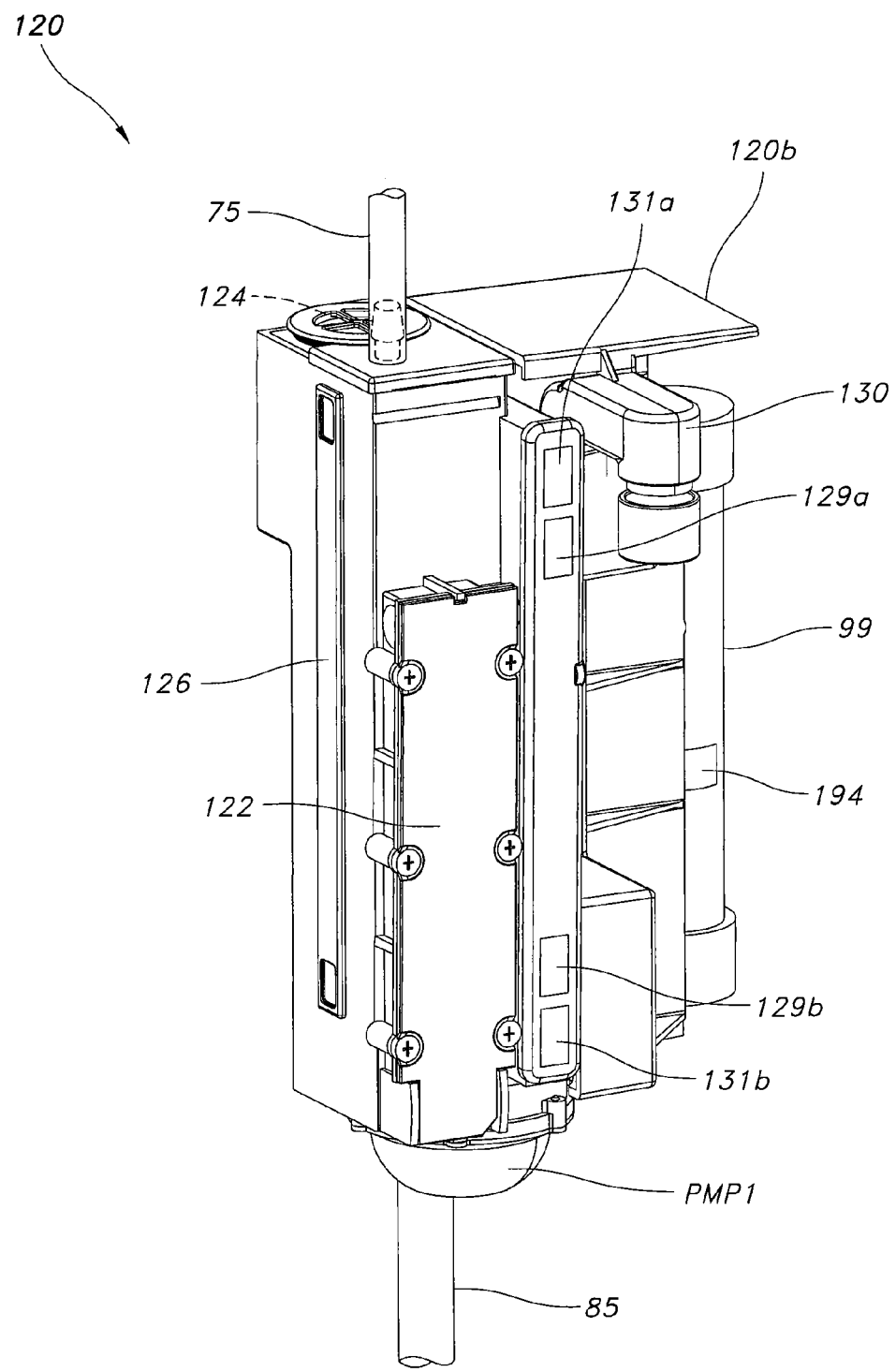
FIG. 10B is rear perspective view of the fluid pathway module shown in FIG. 10A.

Referring to FIGS. 5, and 10B, features and sensors of fluid pathway module 120 are discussed. FIG. 10B illustrates a side view of fluid pathway module 120. Fluid pathway module 120 includes heater HTR1 in the form of heat conduction plate 122 that heats liquid stored in fluid pathway module 120 by receiving thermal energy from heater HTR1. Adjacent heat conduction plate 122 are two temperature reflectors 129*a*, 129*b* that are positioned to align with two infrared temperature sensors IR1, IR2. In an exemplary embodiment, temperature sensor IR1, aligned with temperature reflector 129*a*, monitors the temperature of liquid heated by heat conduction plate 122 and temperature sensor IR2, aligned with temperature sensor reflector 129*b*, monitors the temperature of liquid returning to fluid pathway module 120 from delivery tube 85.

Fluid pathway module 120 includes gas inlet 130 which is configured to receive gas from base unit 110. When fluid pathway module 120 is mounted to base unit 110, as shown in FIG. 3, an air tight seal is formed between gas inlet 130 and gas outlet 649 of base unit chassis 640, shown in FIG. 8C. As shown in FIGS. 5 and 10B, gas received through gas inlet 130 and liquid stored in reservoir 32 flow through passages within fluid pathway module 120 into vapor transfer device 99. Vapor transfer device 99 is mounted to fluid pathway module 120 to form a vapor transfer assembly. Vapor transfer device 99 combines water vapor and gas received from fluid pathway module 120 to form heated and humidified breathing gas. Heated and humidified breathing gas flows from vapor transfer device 99 through outlet 125, shown in FIG. 10A of fluid pathway module 120, and to the patient via delivery tube 85. Exemplary embodiments of vapor transfer devices that may be used with the present invention are disclosed in U.S. patent application Ser. No. 11/851,713, and U.S. patent application Ser. No. 10/810,768, which are both incorporated by reference herein in their entireties.

Indicator 194, such as a barcode or sticker, is positioned on vapor transfer device 99 such that when vapor transfer device 99 is coupled to fluid pathway module 120 and mounted on base unit 110 (FIG. 3), an electronic reader CS1, CS2 aligns with indicator 194. Thus, the type of vapor transfer device 99 installed on fluid pathway module 120 such as a low flow or high flow cartridge, described above, may be determined by a microcontroller (not shown) of humidification system 100.

During operation of humidification system 100, the internal core of vapor transfer device 99 may degrade, resulting in the mixing of gas and water vapor within vapor transfer device 199 becoming less efficient. In this instance, gas pockets may enter the liquid passage of fluid pathway module 120 so that air bubbles form in liquid reservoir 32. In another instance, droplets of liquid may enter the gas passage. These conditions are monitored by bubble sensors BS1, BS2. Bubble sensors BS1, BS2 align with bubble reflectors 131*a*, 131*b* on fluid pathway module 120. In an exemplary embodiment, bubble sensor BS1 aligned with bubble reflector 131*a* monitors air bubble formation within liquid reservoir 32 and bubble sensor BS2 aligned with bubble reflector 131*b* monitors liquid droplets in the gas passage. When the rate at which air bubbles or liquid droplets are detected exceed predefined detection rates, signals may be sent to humidification system microcontroller to generate auditory warnings and illuminate fault icons 115, 112*c* on display panel 105, shown in FIG. 13, to warn a user of these conditions. Additional aspects of warnings and fault icons will be described in further detail below.

Figure 11A:
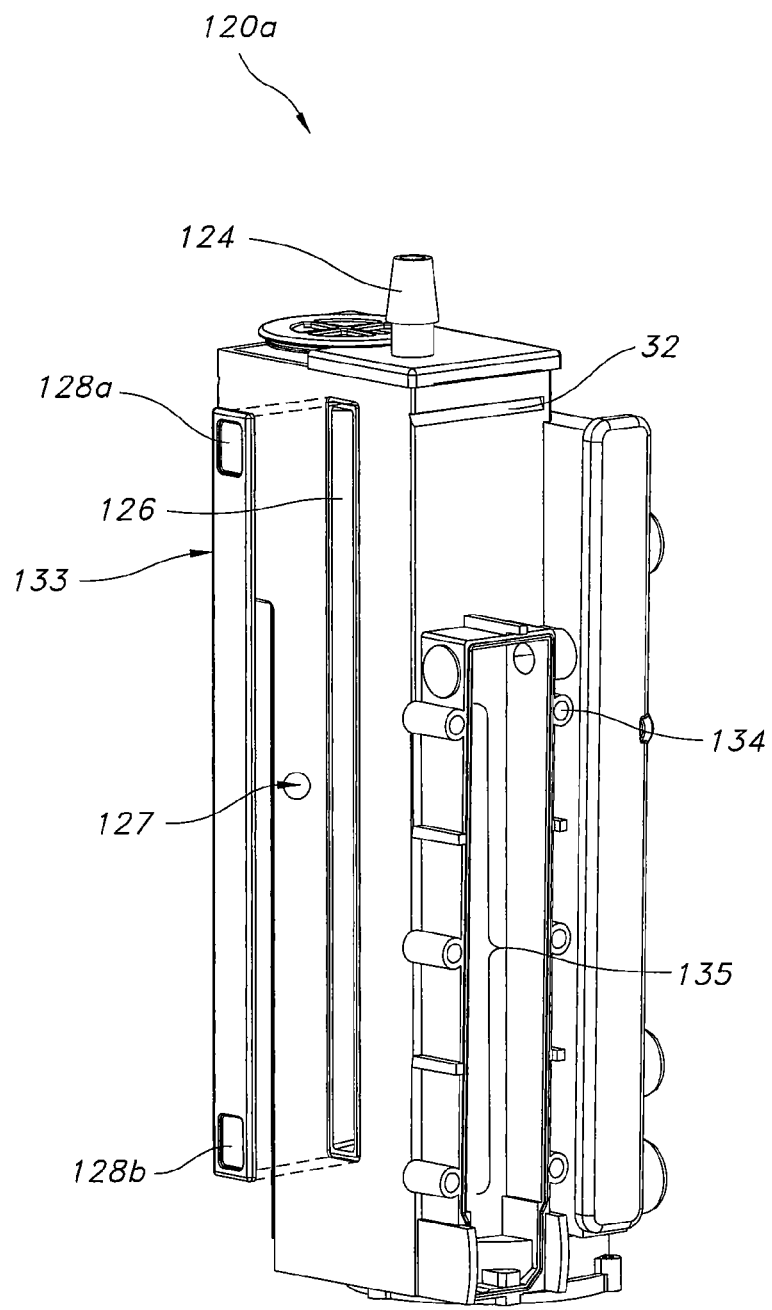
FIG. 11A is an exploded view of the fluid pathway module shown in FIGS. 10A and 10B.
Figure 11B:
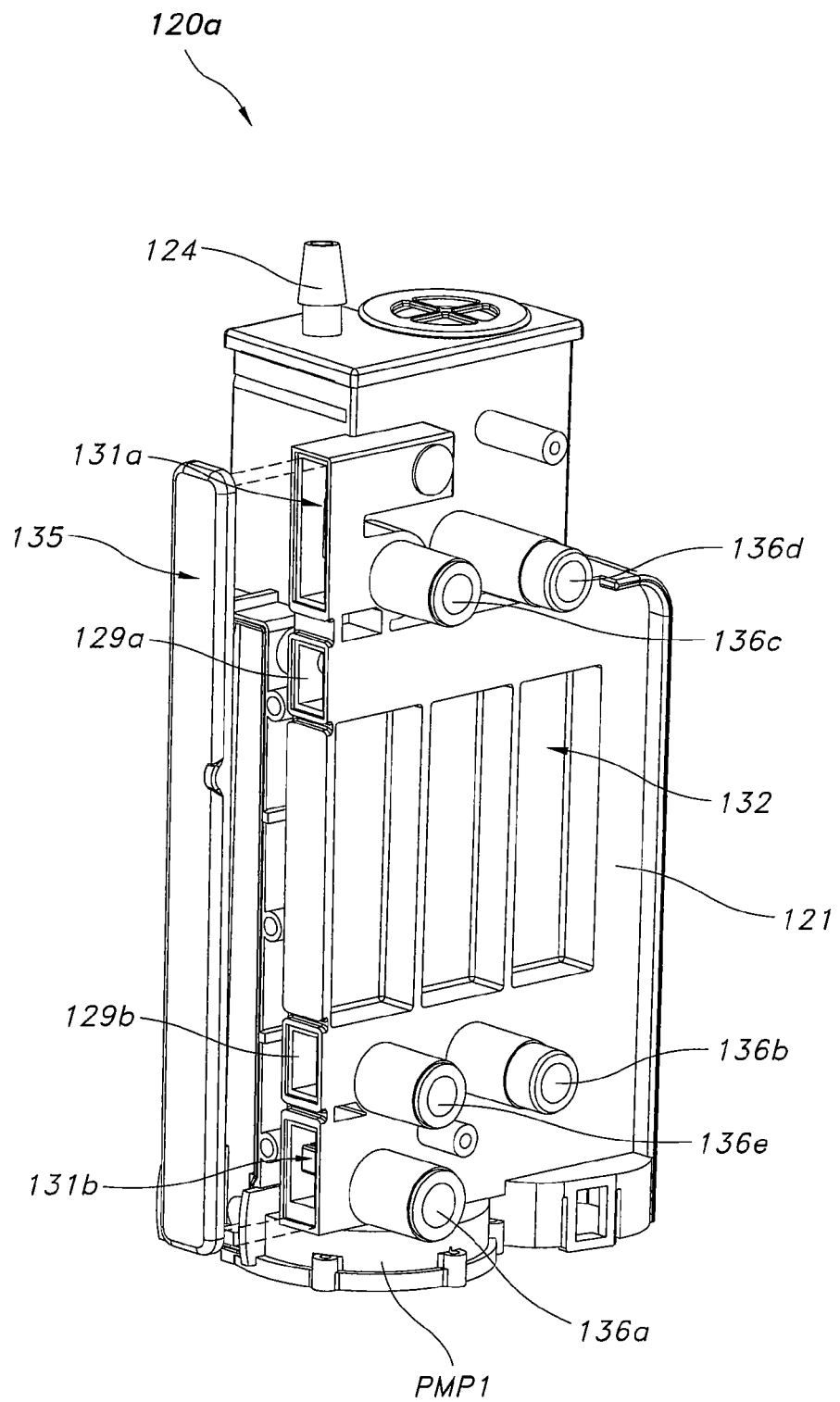
FIG. 11B is another exploded view of the fluid pathway module shown in FIGS. 10A and 10B.

FIGS. 11A and 11B illustrate exploded views of a portion of fluid pathway module 120 shown in FIGS. 10A and 10B. As shown in FIG. 11A, main body 120*a* of fluid pathway module 120 includes liquid reservoir 32 to store liquid received through liquid inlet 124. A water level sensor plate 133 having upper reflector 128*a* and lower reflector 128*b* is configured to be positioned within the reservoir 32 and is visible through sight glass 126. A non-reflective level ball 127 is configured to be positioned within the reservoir 32 such that it floats within reservoir 32 as previously described. Optical water level sensors LS1, LS2 monitor the light reflection from reflectors 128*a*, 128*b*, thereby determining the water level within reservoir 32.

Main body 120*a* of fluid pathway module 120 includes heater HTR1 in the form of a heat conduction plate. Throughout device 100, heat is transferred from heater HTR2, located in base unit 110, to heater HTR1, located in fluid pathway module 120, via conduction. Heat is then transferred by conduction from heater HTR1 to liquid in reservoir 32 when fluid pathway module 120 is mounted to base unit 110. A temperature and bubble sensor plate 135 is adjacent heater portion 134 and is configured to couple with temperature reflectors 129*a*, 129*b* and bubble reflectors 131*a*, 131*b*.

As shown in FIG. 11B, temperature and bubble sensor plate 135 is configured to fit over temperature reflector portions 129*a*, 129*b* and bubble reflector portions 131*a*, 131*b*. Main body 120*a* includes handle 121 which may be used to insert or remove fluid pathway module 120 from base unit 110. Tubular support structures 136*a-e* extend from the side of main body 120*a*. Tubular support structures 136*a-e* are configured to mate with vapor transfer device adapter 120*b*, shown in FIG. 12. In an exemplary embodiment, vapor transfer device 99 is configured to couple to support structures 136*a-c* such that passages defined by support structures 136*a-c* connect with passages of vapor transfer device 99. Liquid and gas may be exchanged through the passages to generate heated and humidified breathing gas in vapor transfer device 99. Heated and humidified breathing gas, for example, may be supplied to gas outlet 125 of fluid pathway module 120, shown in FIG. 10A, through the passage defined by support structure 136*a*. In an exemplary embodiment, heated liquid may be supplied to vapor transfer device 99 through the passage defined by support structure 136c and recycled through the passage defined by support structure 136b.

Figure 12:
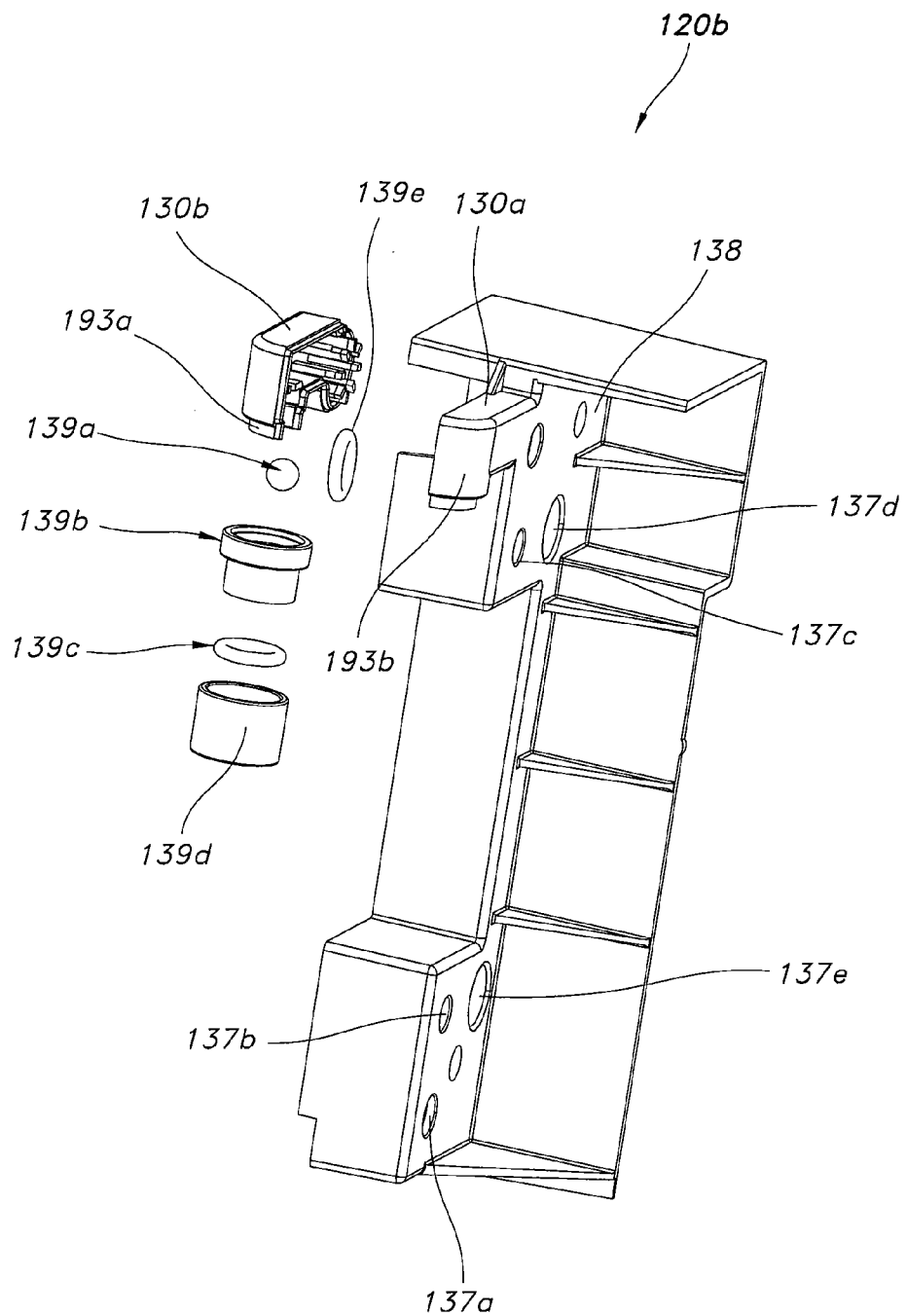
FIG. 12 is an exploded view of the fluid pathway module shown in FIG. 11B.

Referring now to FIGS. 11A and 12, vapor transfer device adapter 120b is configured to couple to main body 120a to fully assemble fluid pathway module 120. Vapor transfer device adapter 120b includes passages 137a-e that are configured to mate with support structures 136a-e of main body 120a.

Referring now also to FIGS. 10A and 10B, vapor transfer device adapter 120b includes gas inlet portion 130a configured to mate with reciprocal gas inlet portion 130b to form gas inlet 130. Gas inlet 130 receives gas from base unit 110 and channels gas to gas opening 138. Gas opening 138 is configured to connect to a gas passage of vapor transfer device 99 and supply gas into vapor transfer device 99. Gas from gas opening 138 and heated water from passage 137c are used in vapor transfer device 99 to generate heated and humidified breathing gas. In an exemplary embodiment, heated and humidified breathing gas exits vapor transfer device 99 through passage 137a and is delivered to breathing gas outlet 125 of fluid pathway module 120. As further shown in FIGS. 5 and 12, excess water in vapor transfer device 99 from passage 137c is recycled back into liquid reservoir 32 through passage 137b.

In an exemplary embodiment, gas inlet 130 includes an air port ball 139a that is configured to be contained within cap 130b. An O-ring 139c is positioned at a distal end of cap 139b and provides a circumferential seal around a distal opening of the cap 139b. Cap cover 139d is positioned distally from O-ring 139c and is configured to seat O-ring 139c when cap cover 139d is secured around a portion of cap 139b. In an embodiment of the present invention, when gas inlet portions 130a, 130b are mated together and coupled to cap 139b and cap cover 139d, the air port ball 130a moves freely between O-ring 139c and distal opening 193a, 193b of gas inlet portions 130a, 130b. In one embodiment, gas flow into gas inlet 130 causes air port ball 139a to move in a direction opposing gravity. When gas flow through gas inlet 130 exceeds gravitational pull on air port ball 139a, air port ball 139a will "float". In another embodiment, when gas is not supplied to gas inlet 130, air port ball 130a will contact and seal O-ring 139c to prevent air flow into gas outlet 649 (FIG. 8C) of base unit chassis 640 (FIG. 8C). Under normal operating conditions, air port ball 139a will "float" between distal opening 193a, 193b and O-ring 139c, thereby providing gas flow through gas opening 138. Thus, as shown in FIGS. 1 and 5, gas only flows in one direction from base unit 110 into fluid pathway module 120.

Referring now to FIG. 10B and FIG. 12, a flexible lip 139e is positioned between gas inlet portions 130a, 130b and adjacent gas opening 138. In one embodiment, when vapor transfer device 99 is coupled to fluid pathway module 120, lip 139e is deformably opened such that gas may flow into vapor transfer device 99. When vapor transfer device 99 is removed from fluid pathway module 120, lip 139e is deformably sealed to prevent air from flowing in a direction from gas opening 138 into the gas outlet 130.

Operation and Display

Figure 13:
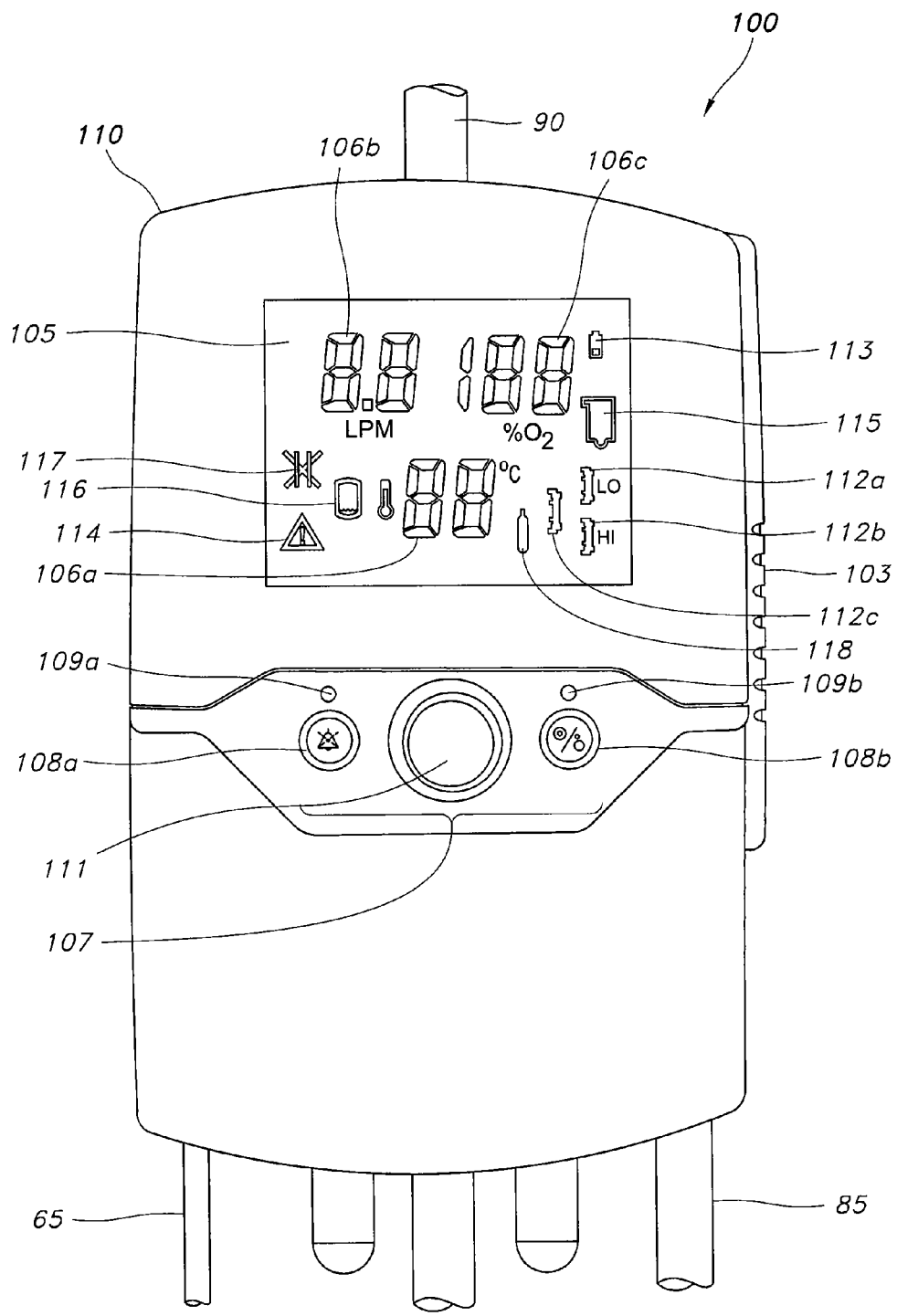
FIG. 13 is a front elevation view of the humidification system according to aspects of the invention.
Figure 14:
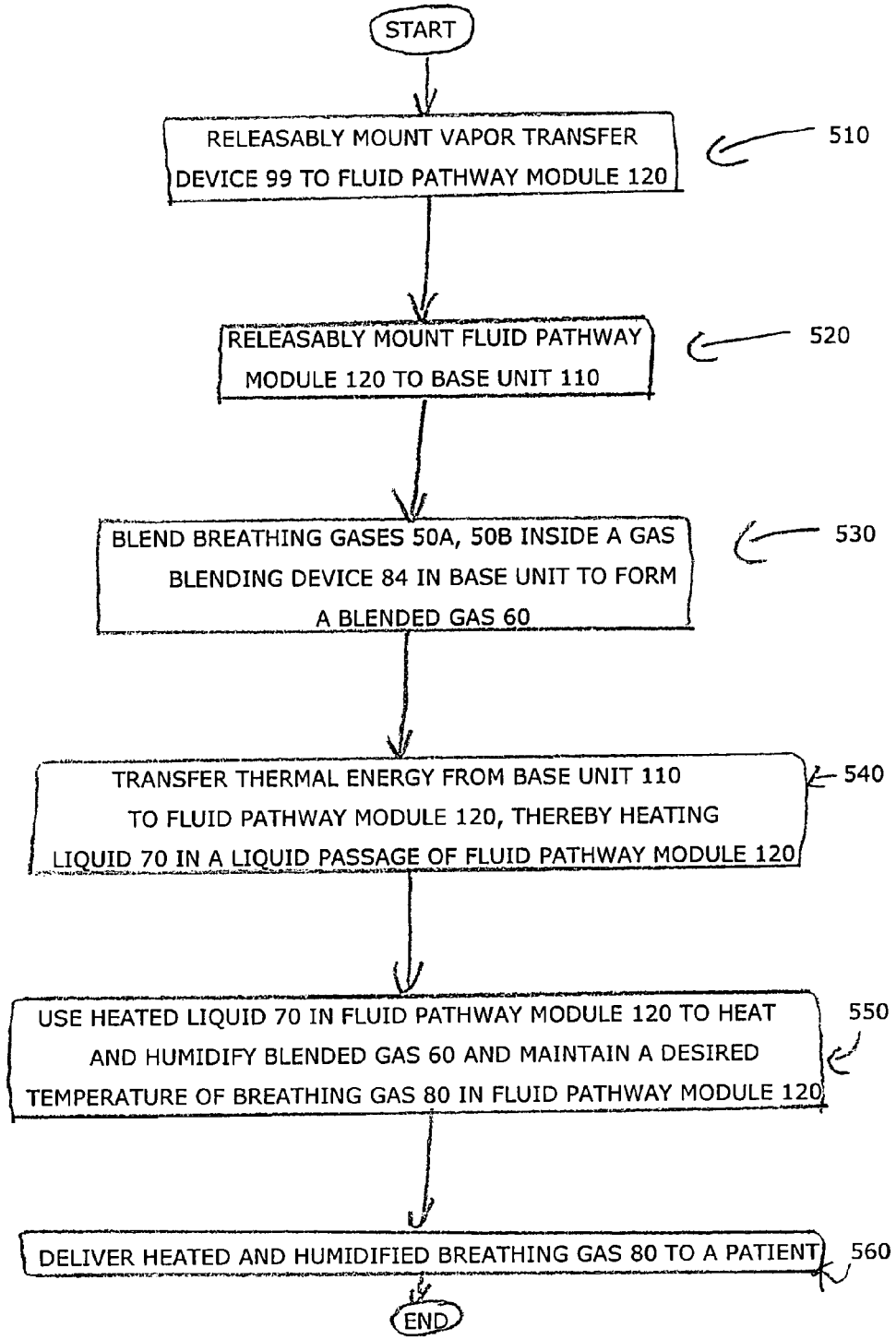
FIG. 14 is a flowchart showing operation of an exemplary embodiment of a humidification system according to the present invention.

Referring now to FIGS. 13 and 14, exemplary aspects of operational modes, warning indicators and a flow chart of the operation of humidification system is 100 are illustrated. Vapor transfer device 99 is releasably mounted to fluid pathway module 120 such that liquid and gas communication is provided between vapor transfer device 99 and fluid pathway module 120 (STEP 510). Fluid pathway module 120 is releasably mounted to base unit 110 such that breathing gas 50a, 50b supplied into base unit 110 flows into fluid pathway module 120 and through vapor transfer device 99 (STEP 520). Breathing gases 50a, 50b are blended inside a gas blending device 84 to form a blended gas 60 (STEP 530). Thermal energy is transferred from base unit 110 to fluid pathway module 120, thereby heating liquid 70 in a liquid passage of fluid pathway module 120 (STEP 540). Liquid 70 is heated in fluid pathway module 120 and is used to heat and humidify blended gas 60 and maintain a desired temperature of breathing gas 80 (STEP 550). Heated liquid 70 and blended gas 60 are passed through vapor transfer device 99, thereby forming heated and humidified breathing gas 80, which is then delivered to a patient (STEP 560), e.g., via a nasal cannula (not shown).

Front panel 104 of base unit 110 includes display panel 105 that provides visual indication of the operating conditions of humidification system 100. In an exemplary embodiment, when AC power is supplied to humidification system 100 through electrical cord 65, battery icon 113 may illuminate on display panel 105 to indicate that an internal battery (not shown) is charging. Battery icon 113 may flash to indicate that the battery backup time is reduced in the event that AC power is lost during charging. When the battery is fully charged, battery icon 113 automatically switches off.

When humidification system 100 is powered on and electrical cord 65 is disconnected from base unit 110, battery icon 113 may illuminate to indicate that DC power is being used. When a loss of AC power occurs in RUN mode, system 100 automatically enters BATTERY mode. In BATTERY mode, heater HTR2 and pump stator STA1 are turned off to conserve battery power. Gas flow control and delivery continues unabated. When AC power is reestablished, system 100 automatically returns to RUN mode. In BATTERY mode, pressing the Run button causes system 100 to enter POWER_OFF mode. If battery capacity is exhausted, system 100 will enter POWER OFF mode.

When humidification system 100 is powered off, pressing the "Standby/Run" button 108b activates an initial boot-up stage that performs a series of self-tests to verify the proper function of subsystems, sensors, and actuators contained in base unit 110. During system boot-up, if any self-test diagnosis fails, a system fault icon 114 is illuminated on display panel 105, and operation of humidification system 100 is disabled. If all self-tests pass, humidification system 100 transitions to "standby" mode and sensors in base unit 110 are activated to detect the presence of fluid pathway module 120 in base unit 110. If fluid pathway module 120 is not detected on base unit 110 or if bubble sensors BS1, BS2 detect that fluid pathway module 120 needs to be replaced, fluid pathway module fault icon 115 is illuminated. In an embodiment of the present invention, when fluid pathway module 120 is mounted to base unit 110, fluid pathway module fault icon 115 is switched off and water level sensors LS1, LS2 in base unit 110 are activated to detect water level in fluid pathway module 120. If the water level is low, a low water icon 116 flashes on/off and an audible alarm sounds to indicate that reservoir 32 of fluid pathway module 120 should be refilled by providing additional water through water supply line 75. If the water is empty, low water icon 116 in constantly illuminated an audible alarm sounds.

When fluid pathway module 120 is mounted to base unit 110, an electronic reader CS1, CS2 is activated to detect the presence of vapor transfer device 99. If vapor transfer device 99 is not detected on fluid pathway module 120 or if bubble sensors BS1, BS2 detect that vapor transfer device 99 is worn, vapor transfer device fault icon 112c is illuminated. In an exemplary embodiment, when vapor transfer device 99 is coupled to fluid pathway module 120 and installed in base unit 110, the type of vapor transfer device 99 installed is determined by electronic reader CS1, CS2. For example, if a high flow vapor transfer device 99 is detected, a high flow icon 112*a* is illuminated on the display panel 105. If a low flow vapor transfer device is detected 99, a low flow icon 112*b* is illuminated. In yet another embodiment, detection of fluid pathway module 120 and vapor transfer device 99 is performed concurrently such that when vapor transfer device 99 is detected, the system automatically determines that fluid pathway module 120 is installed on base unit 110.

Gas flow to the patient is a metered blending of the two input gases, such as medical air and oxygen. A closed feedback control loop exists between the proportional solenoids PSOL1, PSOL2 that control the flow of each gas, and mass flow MFS1, MFS2 sensors that measure the gas flow.

A gas blending algorithm controls the gas blending process. A gas blending algorithm suitable to control the gas blending process will be understood by one having ordinary skill in the art from the description herein. Mass flow sensors MFS1, MFS2 measure the flow rates of medical air and oxygen gases. Proportional solenoids PSOL1, PSOL2 control the flow rates of the gases. Each valve PSOL1, PSOL2 is controlled by a digital to analog converter (DAC), not shown.

A non-linear relationship exists between the output of gas flow sensors MFS1, MFS2 and the corresponding representation in engineering units, such as Standard Liters Per Minute (SLPM). In order to maximize the accuracy of operation and to compensate for part tolerances, a suitable lookup table is provided in the system microprocessor to implement a non-linear transformation function. In one embodiment, the lookup table includes 201 entries that are defined for each of mass flow sensors MFS1, MFS2. The lookup table is indexed by engineering units in 0.25 SLPM increments, and returns values corresponding to the output of mass-flow sensors MFS1, MFS2 in raw 12-bit A/D counts. Fractional indices may be resolved through linear interpolation between table entries.

When system 100 is configured for single gas operation, oxygen saturation level 106*c* is set for 21% for air and 100% for oxygen. An audible alarm sounds if the user attempts to edit or otherwise adjust the value for oxygen saturation level 106*c*. To select single gas operation, the user attaches an air or an oxygen supply to one of gas inlet ports 101*a*, 101*b* while system 100 is in standby mode.

To select dual gas operation, the user attaches gas supply lines to each of gas inlet ports 101*a*, 101*b* while system 100 is in standby mode. If either gas supply loses pressure while system 100 is in dual gas operation, an audible alarm sounds.

It is further contemplated that when any humidification system 100 fault condition exists, auditory warning alarms may be generated. For example, auditory tones and alarms may be generated concurrently when warning indicators are displayed on display panel 105. In another embodiment, alarms may be programmed with unique auditory patterns depending of the priority of the warning. For example, a low priority auditory warning may sound briefly to indicate the occurrence of an event that does not require immediate user attention, whereas a higher priority auditory warning may sound continuously to indicate that immediate attention is required.

Warning alarms may be muted by pressing the mute button 108*a* of the user interface 107. In one embodiment, pressing the mute button 108*a* illuminates LED 109*a* to provide visual indication that warning alarms are muted. In another embodiment, pressing alarm button 108*a* mutes low priority auditory warnings, while higher priority auditory warnings may remain auditory. In yet another embodiment, alarm button 108*a* function may be programmed with additional user adjustable settings such as controlling the brightness of display panel 105. For example, pressing alarm button 108*a* for a period of time may adjust the brightness of display panel 105.

When humidification system 100 is in "standby" mode, user settings such as the temperature 106*a*, flow rate 106*b*, and oxygen saturation level 106*c* of the breathing gas may be adjusted using encoder knob 111 of user interface 107. In exemplary embodiment, pressing encoder knob 111 cycles through user settings that can be adjusted. Pressing the encoder knob 111 once, for example, may activate the temperature adjustment setting and pressing encoder knob 111 in succession may cycle through additional user settings that can be adjusted. In an exemplary embodiment, pressing encoder knob 111 causes the user setting that is activated to blink on display panel 105, thus indicating the specific user setting that may be adjusted. In an exemplary embodiment, rotating encoder knob 111 while in an activated user setting allows the current user setting setpoint to be adjusted. For example, clockwise rotation of encoder knob 111 may increase the setpoint and rotating knob 111 counterclockwise may decrease the setpoint. In another embodiment, encoder knob 111 has an acceleration feature, in which turning knob 111 faster causes the setpoint to increase or decrease in larger steps.

According to one embodiment, after the desired user setting has been set, pressing "Standby/Run" button 108*b* transitions humidification system from "standby" mode to "run" mode. When the system is in "run" mode, status LED 109*b* may be illuminated to indicate that the gas metering and heating operations of the system are activated to deliver heated and humidified gas to the patient. Base unit 110 includes gas pressure sensors to detect if the breathing gas delivery tube 85 is blocked and if gas supply into base unit 110 is too low or too high. A tube fault icon 117 may be lit on display panel 105 when base unit senses a pressure indicating that the breathing gas delivery tube 85 is kinked or blocked. Gas supply fault icon 118 may be displayed when a gas supply problem, such as low or high gas pressure is input to humidification system 100.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. An apparatus for delivering humidified breathing gas to a patient, the apparatus comprising:
   a vapor transfer unit having a liquid passage, a breathing gas passage, a vapor transfer device positioned to transfer vapor to the breathing gas passage from the liquid passage, and a first pump portion within the vapor transfer unit operable to advance liquid through the liquid passage; and
   a base unit that releasably engages the vapor transfer unit to enable reuse of the base unit and selective disposal of the vapor transfer unit, the liquid passage not coupled to the base unit for liquid flow between the base unit and the vapor transfer unit when the vapor transfer unit is received by the base unit;
   wherein the base unit comprises a second pump portion which drives the first pump portion to advance liquid through the liquid passage of the vapor transfer unit when the base unit engages the vapor transfer unit.

2. The apparatus of claim 1, wherein the vapor transfer unit comprises a liquid inlet and a reservoir coupled to the liquid passage, the liquid inlet being configured to transmit liquid from a liquid source into the reservoir and the liquid passage.

3. The apparatus of claim 1, wherein the vapor transfer device is releasably mounted to the vapor transfer unit and positioned to receive liquid and gas from the vapor transfer unit to form said vapor in the vapor transfer device.

4. The apparatus of claim 1, wherein the base unit comprises at least two gas inlets, each gas inlet being configured to receive a gas from respective gas sources and to transmit said gases into a gas blending device to form a blended gas.

5. The apparatus of claim 4, wherein the base unit comprises a gas outlet coupled to the gas blending device to transfer gases to the vapor transfer unit when the vapor transfer unit is releasably mounted to the base unit.

6. The apparatus of claim 5, wherein at least one of the gas inlets further comprises gas blending fins configured to promote laminar gas flow.

7. The apparatus of claim 6, further comprising a plurality of baffles operatively disposed downstream of the gas blending fins to mix gases from each of the two gas inlets.

8. The apparatus of claim 1, wherein the base unit further comprises a self-contained power source.

9. The apparatus of claim 1, wherein
the base unit further comprises at least one sensor positioned to sense a parameter in the liquid passage of the vapor transfer unit.

10. The apparatus of claim 9, wherein the at least one sensor includes at least one cartridge reader and the vapor transfer device comprises an indicator positioned to align with the at least one cartridge reader.

11. The apparatus of claim 9, wherein the at least one sensor comprises a level sensor to sense a full level of liquid in the liquid passage.

12. The apparatus of claim 9, wherein the at least one sensor comprises a level sensor to sense a low level of liquid in the liquid passage.

13. The apparatus of claim 9, wherein the at least one sensor comprises a level sensor to sense an empty liquid passage.

14. The apparatus of claim 1, wherein the first pump portion and the second pump portion are magnetically coupled such that the second pump portion controls pumping of the first pump portion.

15. The apparatus of claim 1, wherein the first pump portion comprises an impeller.

16. The apparatus of claim 15, wherein the second pump portion comprises a stator operationally coupled to the impeller.

17. The apparatus of claim 1, wherein
the vapor transfer unit further comprises a first heater portion positioned to heat liquid in the liquid passage; and
the base unit further comprises a second heater portion adapted to conduct heat to the first heater portion to heat liquid in the liquid passage of the vapor transfer unit.

18. The apparatus of claim 17, wherein the first heater portion and the second heater portion comprise heat conduction plates.

19. The apparatus of claim 17, wherein the first heater portion is adapted to heat a liquid in the vapor transfer unit.

20. The apparatus of claim 1, wherein
the liquid passage defines at least a portion of a liquid circuit, and
the first pump portion is operable to circulate liquid through the liquid portion.

21. An apparatus for delivering humidified breathing gas to a patient, the apparatus comprising:
a vapor transfer unit having a liquid passage, a breathing gas passage, a vapor transfer device positioned to transfer vapor to the breathing gas passage from the liquid passage, and a pump portion within the vapor transfer unit operable to advance liquid through the liquid passage; and
a base unit that releasably engages the vapor transfer unit to enable reuse of the base unit and selective disposal of the vapor transfer unit, the liquid passage not coupled to the base unit for liquid flow between the base unit and the vapor transfer unit when the vapor transfer unit is received by the base unit;
wherein the base unit comprises at least one bubble sensor positioned to sense a parameter in the liquid passage of the vapor transfer unit and the vapor transfer unit comprises at least one reflector for the at least one bubble sensor positioned to align with the at least one bubble sensor in the base unit.

22. An apparatus for delivering humidified breathing gas to a patient, the apparatus comprising:
a vapor transfer unit having a liquid passage, a breathing gas passage, a vapor transfer device positioned to transfer vapor to the breathing gas passage from the liquid passage, and a pump portion within the vapor transfer unit operable to advance liquid through the liquid passage; and
a base unit that releasably engages the vapor transfer unit to enable reuse of the base unit and selective disposal of the vapor transfer unit, the liquid passage not coupled to the base unit for liquid flow between the base unit and the vapor transfer unit when the vapor transfer unit is received by the base unit;
wherein the base unit comprises at least one temperature sensor and the vapor transfer unit comprises a temperature sensor reflector positioned to align with the at least one temperature sensor in the base unit.

* * * * *